US012611440B2

(12) United States Patent
Rosenkilde et al.

(10) Patent No.: US 12,611,440 B2
(45) Date of Patent: Apr. 28, 2026

(54) FUSION PROTEINS AND USES THEREOF

(71) Applicant: SYNKLINO A/S, København K (DK)

(72) Inventors: Mette Marie Rosenkilde, Hellerup (DK); Mads Gravers Jeppesen, Glostrup (DK); Thomas N. Kledal, Lyngby (DK)

(73) Assignee: SYNKLINO A/S, Kobenhavn K. (DK)

( * ) Notice: Subject to any disclaimer, the term of this patent is extended or adjusted under 35 U.S.C. 154(b) by 1045 days.

(21) Appl. No.: 17/639,618

(22) PCT Filed: Sep. 3, 2020

(86) PCT No.: PCT/EP2020/074531
§ 371 (c)(1),
(2) Date: Mar. 2, 2022

(87) PCT Pub. No.: WO2021/043863
PCT Pub. Date: Mar. 11, 2021

(65) Prior Publication Data
US 2022/0288160 A1 Sep. 15, 2022

(30) Foreign Application Priority Data

Sep. 3, 2019 (EP) ..................................... 19195122

(51) Int. Cl.
*A61K 38/16* (2006.01)
*A01N 1/124* (2025.01)
(Continued)

(52) U.S. Cl.
CPC ............ *A61K 38/168* (2013.01); *A01N 1/124* (2025.01); *A61K 31/42* (2013.01); *A61K 31/517* (2013.01);
(Continued)

(58) Field of Classification Search
CPC .... A01N 1/124; A61K 38/168; A61K 38/177; A61K 38/164; A61K 31/522;
(Continued)

(56) References Cited

U.S. PATENT DOCUMENTS

| | | | |
|---|---|---|---|
| 8,592,554 | B2 | 11/2013 | Kledal et al. |
| 9,078,428 | B2 | 7/2015 | Hassanein et al. |

(Continued)

FOREIGN PATENT DOCUMENTS

| | | | | |
|---|---|---|---|---|
| RU | 2616245 C2 | 4/2017 | | |
| WO | WO-2008003327 A2 | * | 1/2008 | .............. A61P 31/18 |

OTHER PUBLICATIONS

Klimstra et al. The Furin Protease Cleavage Recognition Sequence of Sindbis Virus PE2 Can Mediate Virion Attachment to Cell Surface Heparan Sulfate. Journal of Virology (1999), 73(8), 6299-6306. (Year: 1999).*

(Continued)

*Primary Examiner* — Sean C. Barron
(74) *Attorney, Agent, or Firm* — BakerHostetler

(57) ABSTRACT

A fusion protein is provided which comprises a first and a second peptide. The first peptide enables the fusion protein to bind to a receptor expressed on a cell, and the second peptide having a cleavage site that enables the fusion protein to kill said cell. The fusion protein is thus useful for the prevention or treatment of an infection caused by a pathogen. Nucleic acids encoding the fusion protein and methods of making and using the fusion protein are also provided.

21 Claims, 6 Drawing Sheets
Specification includes a Sequence Listing.

(51) Int. Cl.

| | |
|---|---|
| *A61K 31/42* | (2006.01) |
| *A61K 31/517* | (2006.01) |
| *A61K 31/522* | (2006.01) |
| *A61K 31/675* | (2006.01) |
| *A61K 35/17* | (2025.01) |
| *A61K 38/17* | (2006.01) |
| *A61P 31/00* | (2006.01) |
| *A61P 31/22* | (2006.01) |
| *C07K 14/21* | (2006.01) |
| *C07K 14/34* | (2006.01) |
| *C07K 14/415* | (2006.01) |
| *C07K 14/705* | (2006.01) |
| *C07K 14/715* | (2006.01) |

(52) U.S. Cl.
CPC .......... *A61K 31/522* (2013.01); *A61K 31/675* (2013.01); *A61K 35/17* (2013.01); *A61K 38/164* (2013.01); *A61K 38/177* (2013.01); *A61K 38/1793* (2013.01); *A61P 31/00* (2018.01); *A61P 31/22* (2018.01); *C07K 14/21* (2013.01); *C07K 14/34* (2013.01); *C07K 14/415* (2013.01); *C07K 14/705* (2013.01); *C07K 14/7158* (2013.01); *C07K 2319/50* (2013.01); *C07K 2319/55* (2013.01)

(58) Field of Classification Search
CPC .. A61K 31/42; A61K 38/1793; A61K 31/517; A61K 35/17; A61K 31/675; A61P 31/00; A61P 31/22; C07K 14/34; C07K 14/705; C07K 14/415; C07K 14/521; C07K 14/7158; C07K 14/21; C07K 2319/00; C07K 2319/50; C07K 2319/55
See application file for complete search history.

(56) References Cited

U.S. PATENT DOCUMENTS

| | | | |
|---|---|---|---|
| 10,039,276 B2 | 8/2018 | Hassanein et al. | |
| 2010/0048470 A1* | 2/2010 | Kledal | A61K 47/6839 435/243 |

OTHER PUBLICATIONS

Jenny et al. A critical review of the methods for cleavage of fusion proteins with thrombin and factor Xa. Protein Expression and Purification (2003), 31, 1-11; (Year: 2003).*

Burg et al., Structural basis for chemokine recognition and activation of a viral G protein-coupled receptor, Science, 2015, vol. 347, Issue 6226, 6 Pages.

Chiron et al., "Cleavage of Pseudomonas Exotoxin and Diphtheria Toxin by a Furin-like Enzyme Prepared from Beef Liver", The Journal of Biological Chemistry, 1994, vol. 269, No. 27, Issue of Jul. 8, pp. 18167-18176.

Hwnag et al., "Functional domains of pseudomonas exotoxin identified by deletion analysis of the gene expressed in *E. coli*," Cell, Jan. 16, 1987, vol. 48, 1, pp. 129-136.

Krishna et al., "Targeting the latent cytomegalovirus reservoir with an antiviral fusion toxin protein", Nature Communications, Feb. 2, 2017, 9 Pages.

Mizoue et al., Molecular Determinants of Receptor Binding and Signaling by the CX3C Chemokine Fractalkine, The Journal of Biological Chemistry, 2001, vol. 276, No. 36, Issue of Sep. 7, 2001, pp. 33906-33914.

Siegall et a., "Functional analysis of domains II, lb, and III of Pseudomonas exotoxin," Journal of Biological Chemistry, Aug. 25, 1989, vol. 264, No. 24, pp. 14256-14261.

Spiess et al., "Novel Chemokine-Based Immunotoxins for Potent and Selective Targeting of Cytomegalovirus Infected Cells", Journal of Immunology Research, vol. 2017, Jan. 30, 2017, pp. 1-12.

Spiess et al., "Rationally designed chemokine-based toxin targeting the viral G protein-coupled receptor US28 potently inhibits cytomegalovirus infection in Vivo", Proceedings of the National Academy of Sciences, vol. 112, No. 27, Jun. 15, 2015, pp. 8427-8432.

Badri H. et al., "Optimization of radiation dosing schedules for proneural glioblastoma," J Math Bio, vol. 72, Issue 5, 2016, pp. 1301-1336.

Baylot V. et al., "TCTP Has a Crucial Role in the Different Stages of Prostate Cancer Malignant Progression," Results Probl Cell Differ, vol. 64, 2017, pp. 255-261.

Kussie P.H. et al., "A single engineered amino acid substitution changes antibody fine specificity," J Immunol., vol. 152, Issue 1, 1994, pp. 146-152.

Rudikoff S. et al., "Single amino acid substation altering antigen-binding specificity," Proc Natl Acad Sci USA, vol. 79, Issue 6, 1982, pp. 1979-1983.

Yulish Ye.I., "Cytomegalovirus infection in children: treatment approaches in different course of infection," Zdorovie Rebenka/ Children Health, vol. 64, No. 4, 2015, pp. 11-18.

Spiess K. et al.,"Rationally designed chemokine-based toxin targeting the viral G protein-coupled receptor US28 potently inhibits cytomegalovirus infection in Vivo", Proceedings of the National Academy of Sciences, vol. 112, No. 27, Jun. 15, 2015, pp. 8427-8432, Supporting Information, PNAS, 2015.

* cited by examiner 1   2   3   4   5   6   7

FUSION PROTEINS AND USES THEREOF

CROSS-REFERENCE TO RELATED APPLICATIONS

This application is the National Stage of International Patent Application No. PCT/EP2020/074531, filed Sep. 3, 2020, which claims the benefit of European Patent Application No. 19195122.7, filed Sep. 3, 2019, the disclosures of which are incorporated herein by reference in their entireties.

SEQUENCE LISTING

This application contains a Sequence Listing which has been submitted electronically in ASCII format and is hereby incorporated by reference in its entirety. Said ASCII copy, created Mar. 1, 2022, is named 105728 000084 sequence listing.txt and is 42,735 bytes in size.

TECHNICAL FIELD

The present invention relates to a fusion protein which comprises a first and a second peptide. The first peptide enables the fusion protein to bind to a receptor expressed on a cell, which may then internalize, and the second peptide having a cleavage site, with optimized selective properties, which may thus be called an optimized or selective cleavage site that enables the fusion protein to kill said cell. The fusion protein is thus useful for the prevention or treatment of an infection caused by a pathogen, such as a virus, where CMV is an example of such virus. Nucleic acids encoding the fusion protein and methods of making and using the fusion protein are also provided.

BACKGROUND

Immunotoxins are proteins having a targeting portion linked to a toxin. An immunotoxin is an example of a fusion protein. Immunotoxins can be used for the treatment of infections caused by a range of pathogens. For example, toxins linked to antibodies have previously been utilized for targeting CMV-infected cells, albeit with limited success.

Human cytomegalovirus (HCMV) is a species-specific herpesvirus and a significant pathogen particularly in immunocompromised individuals, neonates and patients receiving a transplant.

Currently, all drugs used for the clinical treatment of HCMV infection are associated with considerable adverse side effects. Moreover, the emergence of drug resistance often results in therapy failure.

In addition to pharmacological challenges and poor cell-targeting selectivity with existing immunotoxins, another cause of treatment failure is often an insufficient internalization leading to insufficient killing of infected cells.

These limitations support the value of developing new drug treatments for pathogen-induced infections, such as HCMV.

WO08/003327 discloses immunotoxins useful in treating diseases related to CMV infection. The immunotoxins disclosed therein comprise a variant of the chemokine domain of human CX3CL1 and a toxin.

SUMMARY

The invention is as defined in the claims.

Herein is provided a fusion protein comprising a first peptide providing target selectivity and a second peptide providing a toxin and further providing for internal cleavage of the toxin due to a cleavage site and resulting effector toxicity in the targeted cells. The fusion protein provided herein is useful for the treatment of pathogen-induced infections, including treatment of latent infections.

The present inventors have generated a fusion protein that effectively targets and kills infected cells, such as CMV infected cells, including latently infected cells. This fusion protein comprises a first peptide, which is capable of binding to at least one receptor, which may be a virus-encoded receptor, such as US28, and a second peptide, which comprises an optimized cleavage site and a toxin, such as selected domains of Exotoxin A, e.g. domains II and III. Upon target binding, the receptor is preferably internalized and the second peptide is at least partly cleaved at the cleavage site, thus releasing the toxin part, which then in turn kills the infected cells. Surprisingly, the inventors have found that a certain cleavage site motif (ArgX1X2Arg, wherein X2 is basic such as Arg) corresponding to mutations in the native furin cleavage site of Exotoxin A increase selectivity towards cells expressing pathogen encoded receptors, e.g. US28. This finding allows for improved targeting and killing of infected cells, e.g. CMV infected cells. The optimized cleavage site described herein may thus be utilized for fusion proteins, and in particular immunotoxins, to increase toxicity/cell killing potency and especially selectivity.

In one aspect, the present invention provides a fusion protein comprising:

a) a first peptide which binds at least one receptor expressed on a cell; and b) a second peptide comprising a cleavage site having an amino acid sequence ArgX1X2Arg, wherein X2 is Arg or Lys, and wherein the second peptide comprises a toxin.

In another aspect, the present invention provides an isolated nucleic acid molecule encoding a fusion protein according to the above aspect.

In one aspect, the present invention provides a vector comprising a nucleic acid molecule according to the above aspect.

In another aspect, the present invention provides a recombinant host cell comprising a nucleic acid molecule or a vector according to the above aspects.

In one aspect, the present invention provides a pharmaceutical composition comprising a fusion protein, a nucleic acid, a vector or a recombinant host cell according to the above aspects and a pharmaceutically acceptable carrier, diluent and/or excipient.

In another aspect, the present invention provides a fusion protein, a nucleic acid, a vector, a recombinant host cell or a pharmaceutical composition according to the above aspects for use as a medicament.

In one aspect, the present invention provides a fusion protein, a nucleic acid, a vector, a recombinant host cell or a pharmaceutical composition according to the above aspects for use in the prevention or treatment of an infection caused by a pathogen and/or pathogen associated disorders.

In another aspect, the present invention provides a fusion protein, a nucleic acid, a vector, a recombinant host cell or a pharmaceutical composition according to the above aspects for use in the prevention or treatment of CMV infections and/or CMV-associated disorders.

In one aspect, the present invention provides a method of treating or preventing infection caused by a pathogen such as CMV infections in an individual in need thereof, the method comprising administering a therapeutically effective amount of a fusion protein, a nucleic acid, a vector, a recombinant host cell or a pharmaceutical composition according to any one of the above aspects to the individual.

In another aspect, the present invention provides an ex vivo use of a fusion protein or a pharmaceutical composition according to any one of the above aspects for treatment of solid organs for transplantation and/or hematopoietic stem cells for transplantation.

In one aspect, the present invention provides a fusion protein, a nucleic acid, a vector, a host cell or a pharmaceutical composition according to the above aspects for use in the manufacture of a medicament for the prevention or treatment of an infection caused by a pathogen and/or pathogen associated disorders, such as for the prevention or treatment of CMV infections and/or CMV-associated disorders.

In another aspect, the present invention provides a method for producing a fusion protein according to any one of the above aspects, the method comprising culturing a host cell as defined in any of the above aspects under conditions which permit expression of the encoded fusion protein.

A. Schematic diagram of the domain structure of; human $CX_3CL1$ (S=signal sequence, $CX_3CL1$=chemokine domain, Stalk=Mucin-like stalk, M=Membrane spanning part and C=cytoplasmic domain, *Pseudomonas aeruginosa* Exotoxin A (S=signal sequence, Domain I=receptor binding domain, Domain II=translocation domain, Ib=Domain Ib with unknown function and Domain III=ADP-ribosylating domain), Amino acid numbering for the precursor protein is given above each protein. Disulphide bridges are indicated below each protein with a square bracket along with numbering of the amino acids involved. B. Schematic diagram of SYN002. A mutation in a given domain is written in single letter code of the amino acid involved along with its number. E.g. P303R means that proline at position number 303 has been substituted with arginine. Single letter code is also used at the N- and C-terminus of the constructs and between domains. A dashed line between two domains indicates that the amino acids are connected. Furin cleaves between amino acids 304 and 305 of domain II of Exotoxin A.

Figure 1:
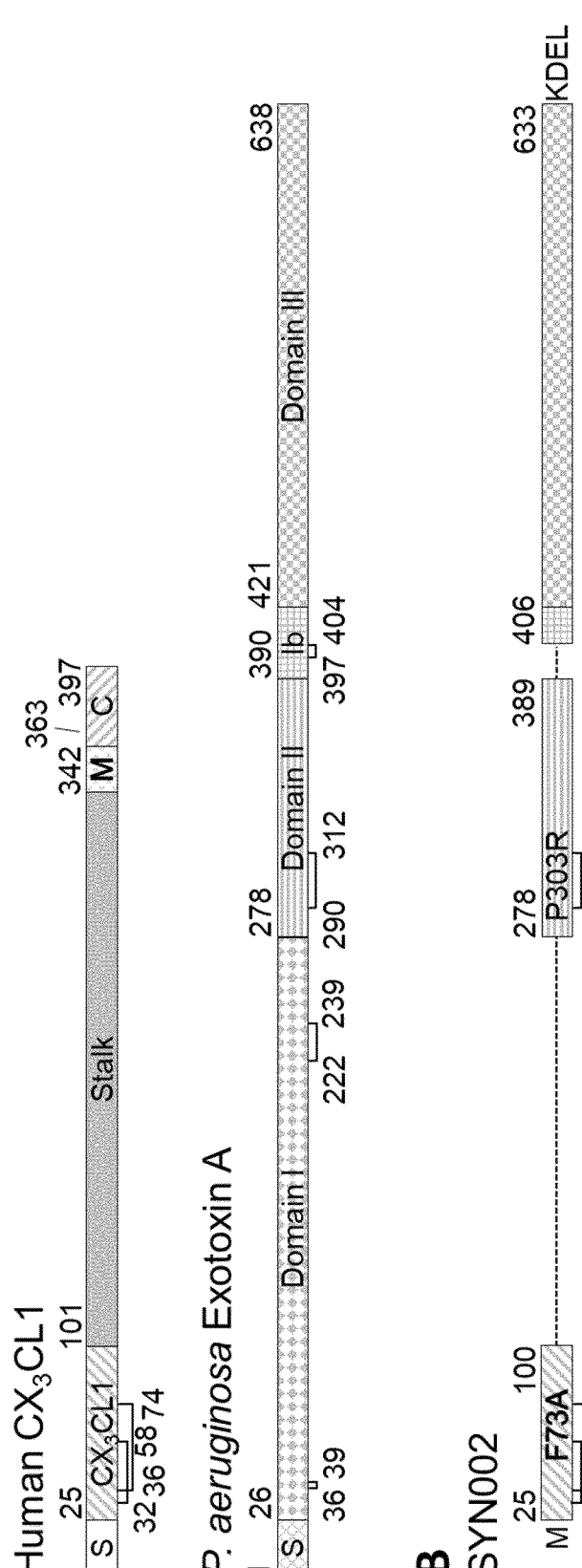
FIG. 1: Domain structures of an exemplary first peptide being human CX3CL1, *Pseudomonas* Exotoxin A and fusion protein SYN002.
Figure 2:
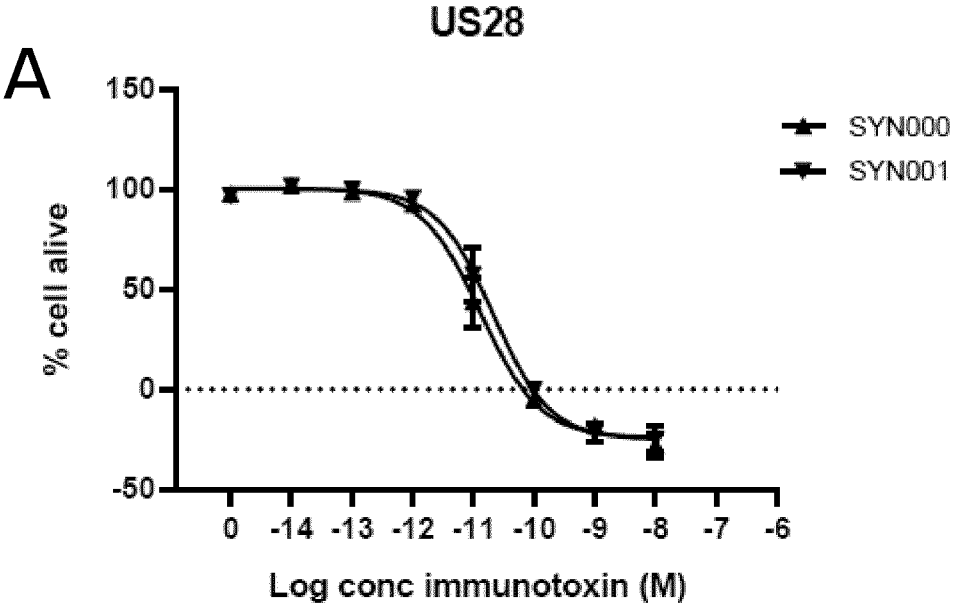
Figure 2:
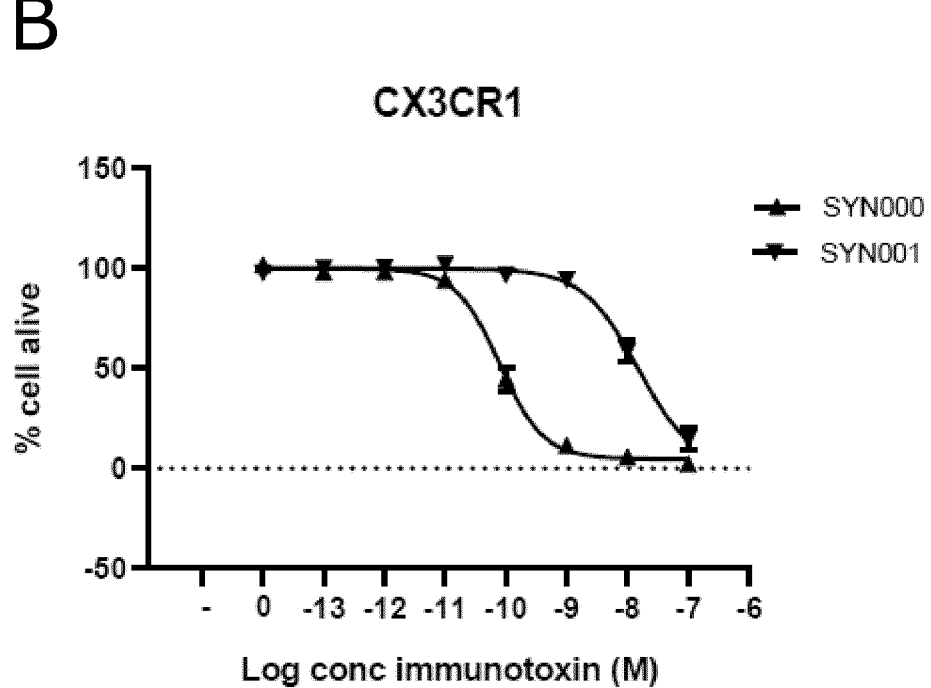

FIG. 2: Selectivity due to F49A mutation.

Substituting a single amino acid in the chemokine part of SYNx leads to selectivity towards the US28 receptor (A) compared to the CXCR1 receptor (B). SYN000 is the wild type human chemokine (C-X3-C motif) ligand 1 (CX3CL1) (native chemokine sequence) while SYN001 has a single mutation (F49A) in the receptor binding part of the protein.

Figure 3:
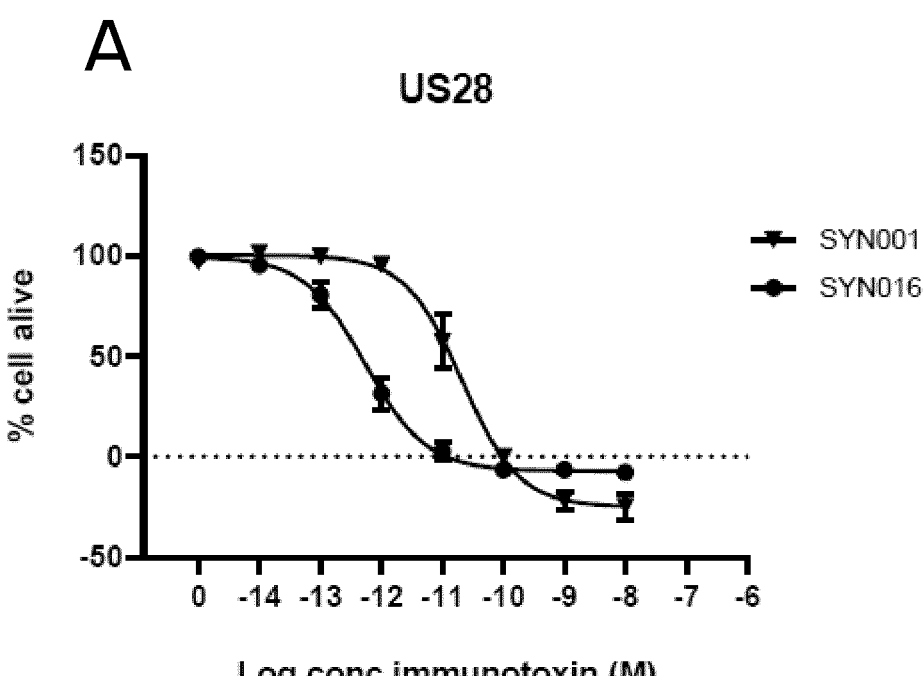
Figure 3:
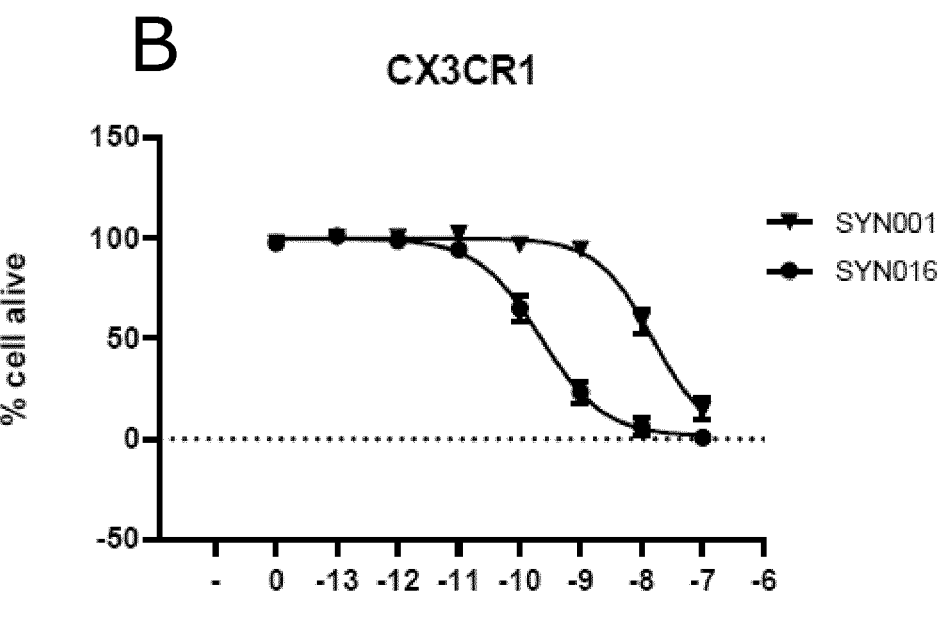

FIG. 3: Introducing a Furin cleavage site (in this case full length translocation domain of Exotoxin A) increases potency.

Adding the full length translocation domain of Exotoxin A comprising a furin cleavage site to the SYN001 construct, yielding SYN016, increases the potency on both the endogenous CX3CR1- and virus encoded US28-receptor expressing cells.

Figure 4:
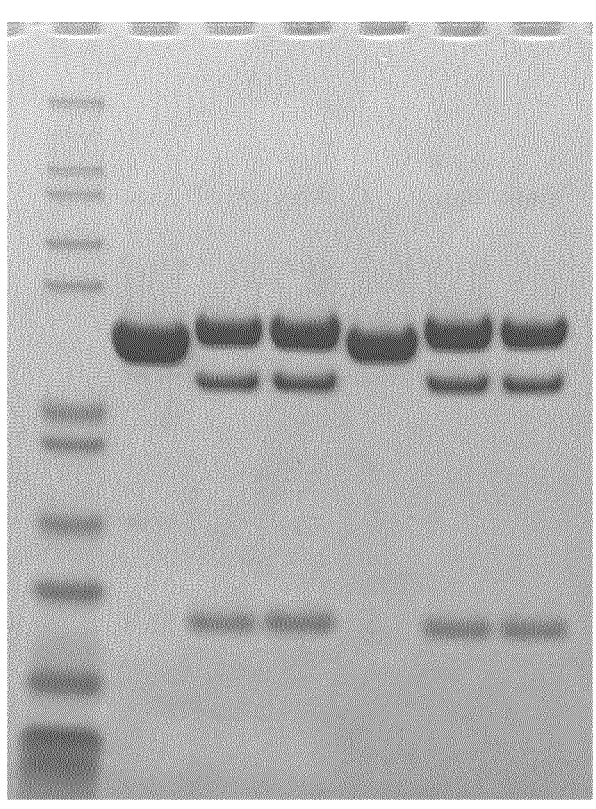

FIG. 4: In vitro cleavage by Furin.

in vitro cleavage by Furin of the SYN002-construct, which has the optimized cleavage site (RQRR), compared to a fusion protein construct SYN016 with the native furin cleavage site sequence (RQPR) does not yield an improvement. In vitro Furin digest of SYNx. Lane 1; Mark 12 protein standard, lane 2; SYN000, lane 3; SYN017, lane 4; SYN014, lane 5; SYN001, lane 6; SYN016 and lane 7; SYN002. SYN000, SYN017 and SYN014 has native CX3CL1 chemokine sequence, while SYN001, SYN016 and SYN002 has F49A mutation in chemokine part. SYN000, SYN017, SYN001 and SYN016 has native Furin cleavage site (RQPR) while SYN014 and SYN002 have optimized cleavage site (RQRR).

Figure 5:
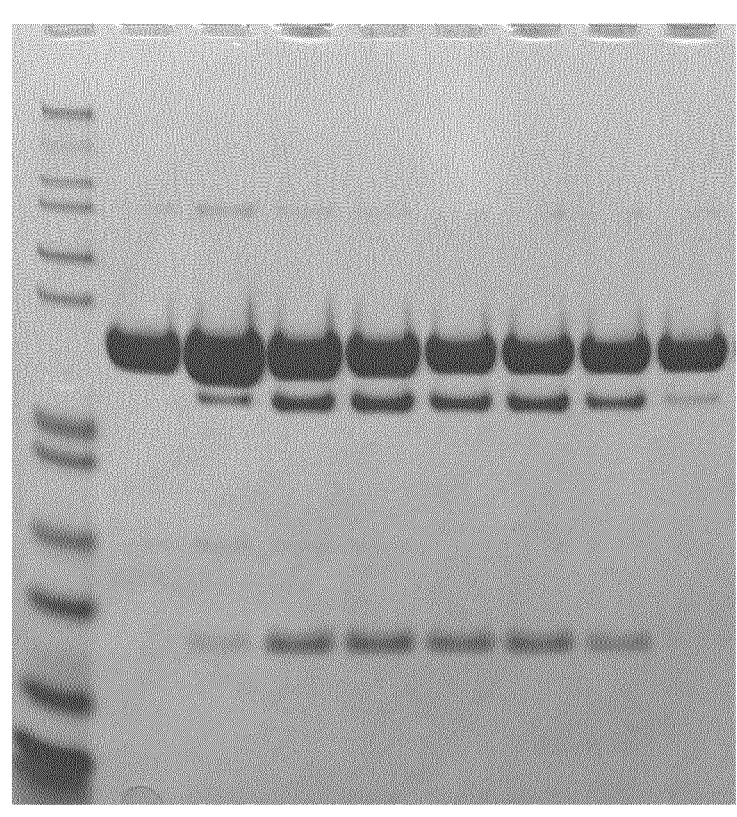

FIG. 5: SYN002 is cleaved by Furin over a wide pH range.

SYN002 was cleaved in vitro over a wide pH range. Lane 1; Mark 12 protein standard, lane 2; No Furin added, lane 3; +8 mM HCl (approx. pH 5.2), lane 4; +6 mM HCl (approx. pH 6.3), lane 5; +4 mM HCl (approx. pH 6.6), lane 6; +2 mM HCl (approx. pH 7.0), lane 7; no titrant added (approx. pH 7.4), lane 8; 2 mM NaOH (approx. pH 7.7) and lane 9; +4 mM NaOH (approx. pH 9.0).

Figure 6:
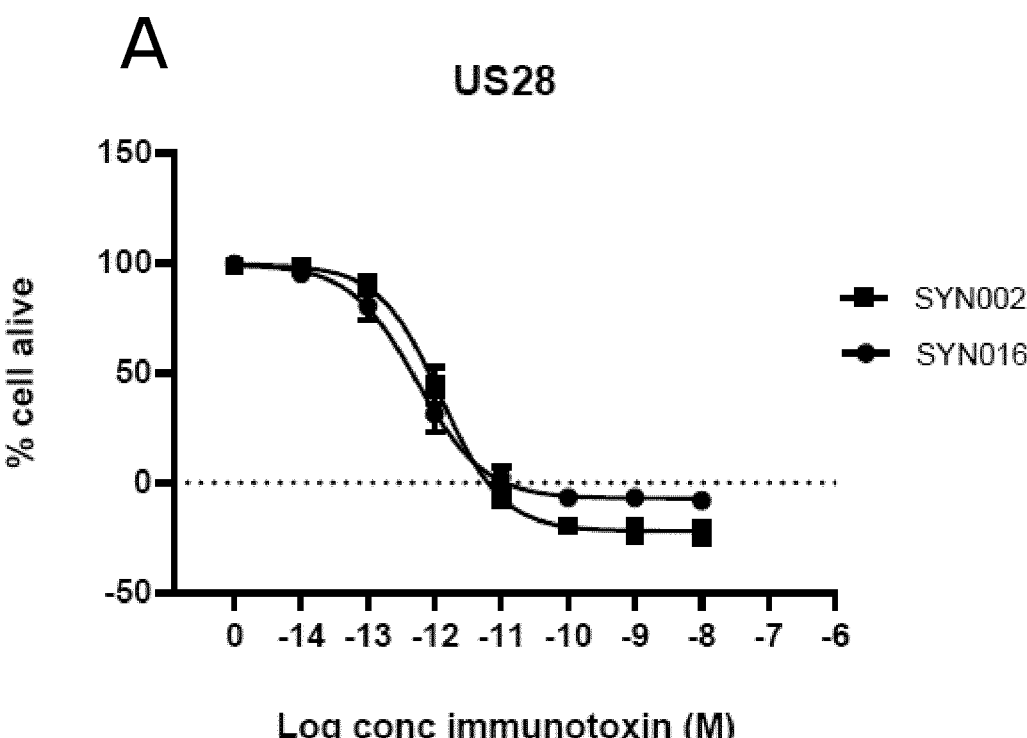
Figure 6:
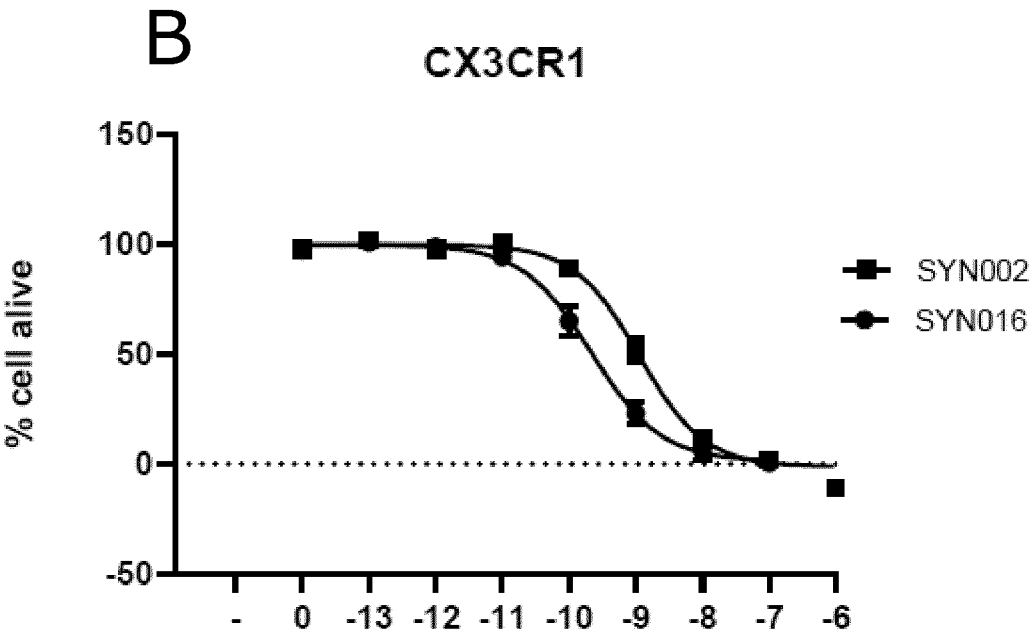

FIG. 6: The optimized cleavage site increases selectivity

When introducing an optimized cleavage site ArgX1X2Arg into the second peptide, in this particular case the optimized cleavage site ArgGlnArgArg into SYN016 to give SYN002, an increase in selectivity towards the virus encoded receptor is obtained. For SYN002 on cells expressing a virus encoded receptor such as US28 in the cell killing potency is approximately maintained compared to SYN016 having an cleavage site ArgGlnProArg (thus X2=Pro), however the potency on cells expressing an endogenous/human receptor such as CX3CR1 is decreased compared to SYN016. Both selectivity and potency are increased when comparing to a second peptide not comprising a furin cleavage site e.g. SYN000 (not shown in figure).

DETAILED DESCRIPTION

The present disclosure relates to a fusion protein comprising a first peptide providing target recognition and target selectivity and a second peptide providing a toxin and further providing for intracellular cleavage and release of the toxin and resulting effector toxicity in the targeted cells. The fusion protein provided herein is useful for the treatment of pathogen-induced infections, including treatment of latent infections.

The present inventors have generated a fusion protein that effectively targets and kills infected cells, such as CMV infected cells including latently infected cells, upon binding to a receptor, e.g. a receptor encoded by a virus, such as a US28, which may be advantageously constitutively internalized.

US28 is a G protein coupled receptor encoded by human cytomegalovirus open reading frame US28. US28 is a constitutively internalizing receptor. Thus, chemokines or other compounds that binds US28 are internalized into the cell that express the receptor. US28 is expressed on CMV infected cells including cells latently infected with CMV.

The fusion protein comprises a first peptide, which is capable of binding to a receptor, especially receptors encoded by a pathogen, such as US28, and a second peptide which comprises an optimized cleavage site and a toxin, such as selected domains of Exotoxin A. The selectivity towards pathogen encoded receptors, such as US28, of the fusion protein is surprisingly enhanced following mutations in the cleavage site.

The optimized cleavage site described herein may be utilized for a variety of fusion proteins, and in particular immunotoxins, to increase cell killing selectivity, by altering cell killing potency in a target receptor selective manner.

In one aspect the present invention provides a fusion protein comprising:

a) a first peptide which binds at least one receptor expressed on a cell; and b) a second peptide comprising a cleavage site having an amino acid sequence ArgX1X2Arg, wherein X2 is Arg or Lys, and wherein the second peptide comprises a toxin.

The term "amino acid" as used herein includes the standard twenty genetically-encoded amino acids and their corresponding stereoisomers in the D' form (as compared to the natural 'ʟ' form), omega-amino acids and other naturally-occurring amino acids, unconventional amino acids (e.g. α,α-disubstituted amino acids, N-alkyl amino acids, etc.) and chemically derivatised amino acids. When an amino acid is being specifically enumerated, such as "alanine" or "Ala" or "A", the term refers to both ʟ-alanine and ᴅ-alanine unless explicitly stated otherwise.

In an embodiment of the invention, the fusion protein only consists of naturally occurring amino acids.

Cleavage Site

The second peptide of the present disclosure comprises a cleavage site having the amino acid sequence ArgX1X2Arg X1 may be any amino acid. In one embodiment, X1 is selected from the group consisting of Gln, Ser, Thr and Asn. In one embodiment X1 is Gln.

X2 is selected from Arg and Lys. In an advantageous embodiment X2 is Arg. In one embodiment, X2 is Lys. By introducing a basic amino acid, such as Arg at amino acid position X2, the cell killing selectivity is enhanced. Such that e.g. virus infected cells expressing a receptor encoded by the virus and binding the first peptide, are killed more efficiently than e.g. cells expressing an endogenous receptor, which may also bind the first peptide.

In a preferred embodiment, the cleavage site comprises or consists of the amino acid sequence ArgGlnArgArg (RQRR). In one embodiment, the cleavage site comprises or consists of the amino acid sequence ArgGlnLysArg. In one embodiment, the cleavage site comprises or consists of the amino acid sequence ArgSerLysArg. In one embodiment, the cleavage site comprises or consists of the amino acid sequence ArgSerArgArg. In one embodiment, the cleavage site comprises or consists of the amino acid sequence ArgThrLysArg. In one embodiment, the cleavage site comprises or consists of the amino acid sequence ArgThrArgArg. In one embodiment, the cleavage site comprises or consists of the amino acid sequence ArgAsnLysArg. In one embodiment, the cleavage site comprises or consists of the amino acid sequence ArgAsnArgArg.

In one embodiment, cleavage is occurring at the C-terminal end of the cleavage site.

It may be possible to cleave the fusion protein with furin, however other enzymes or proteases may also be involved in cleavage at the cleavage site.

Thus, in one embodiment, the cleavage site is an enzymatic cleavage site.

In one embodiment, the enzymatic cleavage site is a furin cleavage site.

Receptor

In one embodiment, the first peptide binds to at least one receptor expressed on a cell. In one embodiment, the first peptide binds to at least two receptors expressed on a cell.

In one embodiment, one receptor binding the first peptide is a receptor encoded by a pathogen and a further receptor binding the first peptide is a human encoded receptor and/or endogenous receptor for the first peptide or a variant thereof.

In one embodiment, the receptor is a G-protein coupled receptor (GPCR), such as US28 of SEQ ID NO: 10.

In on embodiment, the receptor is a chemokine receptor. In one embodiment, the chemokine receptor is a CC chemokine receptor and/or a CX3C chemokine receptor.

In one embodiment, the CC chemokine receptor is US28. In one embodiment, the CX3C chemokine receptor is CX3CR1.

In one embodiment, the receptor is encoded by a pathogen. In one embodiment, the pathogen is a bacteria. In one embodiment, the pathogen is a virus. In one embodiment, the virus is a DNA virus. In one embodiment, the virus is a RNA virus. In one embodiment, the virus is a herpesvirus. In one embodiment, the virus is cytomegalovirus.

In one embodiment, the receptor is capable of internalizing. In one embodiment, the receptor is internalized upon binding to the first peptide. In one embodiment, the receptor is constitutively internalized. The receptor encoded by a pathogen is advantageously constitutively internalized as this will ensure efficient uptake of the fusion protein by the pathogen infected cell and thereby the death of the infected cell with a minimum of unwanted toxicity and side effects. "Internalization" refers to the process of a receptor being moved into the cell that it is expressed on. For example, the receptor might enter the cell by endocytosis or phagocytosis.

In some embodiments, the present invention provides a fusion protein that targets a specific cell by binding in a selective manner to a receptor leading to the internalization of said receptor. The toxin part of the fusion protein is then cleaved and said cell is killed.

Toxin

In one embodiment, the fusion protein is an immunotoxin. An "immunotoxin" refers to a protein consisting of a targeting portion linked to a toxin. The targeting portion may also be called a ligand.

The toxin may be different kinds of toxins. In one embodiment, the second peptide comprises a toxin selected from the group consisting of *Pseudomonas* Exotoxin A, gelonin, bouganin, saporin, ricin, ricin A chain, bryodin, restrictocin, diphteria toxin, diphteria toxin A chain and variants and fragments thereof. The toxin part of the fusion protein enables the killing of the cells. The toxin is cytotoxic.

In one embodiment, the second peptide comprises one or more domains of *Pseudomonas* Exotoxin A. In one embodiment, the second peptide comprises at least a part of the Exotoxin A of SEQ ID NO: 9.

The Fusion Protein

The first peptide is a targeting moiety, which allows for binding to a receptor expressed on a cell.

In one embodiment, the first and the second peptide are operably linked. Generally, "operably linked" means that the sequences being linked are contiguous and/or placed into a functional relationship with each other, such as covalently linked.

In one embodiment, the first peptide comprises or consists of a. an amino acid sequence of SEQ ID NO: 1;

b. a variant of SEQ ID NO: 1 comprising or consisting of an amino acid sequence with at least 80% sequence identity to the amino acid sequence of SEQ ID NO: 1, more preferably at least 85% or 90% sequence identity to SEQ ID NO: 1, and most preferably at least 95%, 96%, 97%, 98% or 99% identity to SEQ ID NO: 1;

c. a fragment of SEQ ID NO: 1 being more than 50 amino acids in length, such as more than 60, 70, or 75 amino acids in length, or a variant thereof with at least 80% sequence identity to the amino acid sequence of SEQ ID NO: 1, more preferably at least 85% or 90% sequence identity to SEQ ID NO: 1, and most preferably at least 95%, 96%, 97%, 98% or 99% identity to SEQ ID NO: 1.

In one embodiment the first peptide comprises or consists of a variant of SEQ ID NO: 1 comprising or consisting of an amino acid sequence with at least 90% sequence identity to the amino acid sequence of SEQ ID NO: 1. In one embodiment the first peptide comprises or consists of a variant of SEQ ID NO: 1 comprising or consisting of an amino acid sequence with at least 95% sequence identity to the amino acid sequence of SEQ ID NO: 1. In one embodiment the first peptide comprises or consists of a variant of SEQ ID NO: 1 comprising or consisting of an amino acid sequence with at least 96% sequence identity to the amino acid sequence of SEQ ID NO: 1. In one embodiment the first peptide comprises or consists of a variant of SEQ ID NO: 1 comprising or consisting of an amino acid sequence with at least 97% sequence identity to the amino acid sequence of SEQ ID NO: 1. In one embodiment the first peptide comprises or consists of a variant of SEQ ID NO: 1 comprising or consisting of an amino acid sequence with at least 98% sequence identity to the amino acid sequence of SEQ ID NO: 1. In one embodiment the first peptide comprises or consists of a variant of SEQ ID NO: 1 comprising or consisting of an amino acid sequence with at least 99% sequence identity to the amino acid sequence of SEQ ID NO: 1.

In one embodiment the first peptide comprises or consist of a fragment of SEQ ID NO: 1 being more than 50 amino acids in length. In one embodiment the first peptide comprises or consist of a fragment of SEQ ID NO: 1 being more than 60 amino acids in length. In one embodiment the first peptide comprises or consist of a fragment of SEQ ID NO: 1 being more than 70 amino acids in length. In one embodiment the first peptide comprises or consist of a fragment of SEQ ID NO: 1 being more than 75 amino acids in length.

In one embodiment the first peptide comprises or consist of a fragment of SEQ ID NO: 1, or a variant thereof with at least 80% sequence identity to the amino acid sequence of SEQ ID NO: 1. In one embodiment the first peptide comprises or consist of a fragment of SEQ ID NO: 1, or a variant thereof with at least 85% sequence identity to the amino acid sequence of SEQ ID NO: 1. In one embodiment the first peptide comprises or consist of a fragment of SEQ ID NO: 1, or a variant thereof with at least 90% sequence identity to the amino acid sequence of SEQ ID NO: 1. In one embodiment the first peptide comprises or consist of a fragment of SEQ ID NO: 1, or a variant thereof with at least 95% sequence identity to the amino acid sequence of SEQ ID NO: 1. In one embodiment the first peptide comprises or consist of a fragment of SEQ ID NO: 1, or a variant thereof with at least 96% sequence identity to the amino acid sequence of SEQ ID NO: 1. In one embodiment the first peptide comprises or consist of a fragment of SEQ ID NO: 1, or a variant thereof with at least 97% sequence identity to the amino acid sequence of SEQ ID NO: 1. In one embodiment the first peptide comprises or consist of a fragment of SEQ ID NO: 1, or a variant thereof with at least 98% sequence identity to the amino acid sequence of SEQ ID NO: 1. In one embodiment the first peptide comprises or consist of a fragment of SEQ ID NO: 1, or a variant thereof with at least 99% sequence identity to the amino acid sequence of SEQ ID NO: 1.

In one embodiment, the amino acid residue of SEQ ID NO:1 in position 49 is mutated to an Ala, a Lys or an Asp, preferably Ala. Theses substitutions may lead to increased cell killing selectivity towards cells expressing a pathogen encoded receptor binding the first peptide compared to a human or endogenous encoded receptor also binding the first peptide.

In one embodiment, the first peptide further comprises a Methionine (M) at the N-terminus.

In one embodiment, the first peptide comprises or consists of one or more additional amino acids, inserted at the N- and/or C-terminus and/or internally within the amino acid sequence of SEQ ID NO:1.

In one embodiment, one or more amino acids are deleted at the N- and/or C-terminus and/or internally within the amino acid sequence of SEQ ID NO:1.

In one embodiment, the first peptide is less than 100 amino acids in length.

In one embodiment the first peptide is less than 90 amino acids in length.

In one embodiment the first peptide is less than 85 amino acids in length.

In one embodiment the first peptide is less than 80 amino acids in length.

In one embodiment, the second peptide comprises a domain A, which may be a translocation domain, such as a domain A having an amino acid sequence according to SEQ ID NO:3 or a fragment or variant thereof, and/or a domain B, such as a domain B having an amino acid sequence according to SEQ ID NO:4 or a fragment or variant thereof, and/or a domain C, which may be a cytotoxic domain, such as a domain C having an amino acid sequence according to SEQ ID NO:5 or a fragment or variant thereof.

In one embodiment, the second peptide comprises a domain A, such as a domain A having an amino acid sequence according to SEQ ID NO:3 or a fragment or variant thereof. In one embodiment, the second peptide comprises a domain A, such as a domain A having an amino acid sequence according to SEQ ID NO:3 or a fragment or variant thereof, and a domain B, such as a domain B having an amino acid sequence according to SEQ ID NO:4 or a fragment or variant thereof. In one embodiment, the second peptide comprises a domain A, such as a domain A having an amino acid sequence according to SEQ ID NO:3 or a fragment or variant thereof, and a domain B, such as a domain B having an amino acid sequence according to SEQ ID NO:4 or a fragment or variant thereof, and a domain C such as a domain C having an amino acid sequence according to SEQ ID NO:5 or a fragment or variant thereof. In one embodiment, the second peptide comprises a domain B having an amino acid sequence according to SEQ ID NO:4 or a fragment or variant thereof. In one embodiment, the second peptide comprises a domain C, such as a domain C having an amino acid sequence according to SEQ ID NO:5 or a fragment or variant thereof.

In one embodiment, the second peptide comprises a. an amino acid sequence of SEQ ID NO: 3;

b. a variant of SEQ ID NO: 3 comprising or consisting of an amino acid sequence with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3;

c. a fragment of SEQ ID NO: 3 being more than 80 amino acids in length, such as more than 90, 100, or 110 amino acids in length, or a variant thereof with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3.

In one embodiment, the second peptide comprises a. an amino acid sequence of SEQ ID NO: 4;

b. a variant of SEQ ID NO: 4 comprising or consisting of an amino acid sequence with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4;

c. a fragment of SEQ ID NO: 4 being more than 6 amino acids in length, such as more than 8, 10, or 12 amino acids in length, or a variant thereof with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4.

In one embodiment, the second peptide comprises a. an amino acid sequence of SEQ ID NO: 5;

b. a variant of SEQ ID NO: 5 comprising or consisting of an amino acid sequence with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5;

c. a fragment of SEQ ID NO: 5 being more than 180 amino acids in length, such as more than 190, 200, or 210 amino acids in length, or a variant thereof with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5.

In one embodiment, the second peptide comprises a. an amino acid sequence of SEQ ID NO: 3;

b. a variant of SEQ ID NO: 3 comprising or consisting of an amino acid sequence with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3;

c. a fragment of SEQ ID NO: 3 being more than 80 amino acids in length, such as more than 90, 100, or 110 amino acids in length, or a variant thereof with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3; and d. an amino acid sequence of SEQ ID NO: 4;

e. a variant of SEQ ID NO: 4 comprising or consisting of an amino acid sequence with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4;

f. a fragment of SEQ ID NO: 4 being more than 6 amino acids in length, such as more than 8, 10, or 12 amino acids in length, or a variant thereof with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4.

In one embodiment, the second peptide comprises a. an amino acid sequence of SEQ ID NO: 3;

b. a variant of SEQ ID NO: 3 comprising or consisting of an amino acid sequence with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3;

c. a fragment of SEQ ID NO: 3 being more than 80 amino acids in length, such as more than 90, 100, or 110 amino acids in length, or a variant thereof with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3; and d. an amino acid sequence of SEQ ID NO: 4;

e. a variant of SEQ ID NO: 4 comprising or consisting of an amino acid sequence with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4;

f. a fragment of SEQ ID NO: 4 being more than 6 amino acids in length, such as more than 8, 10, or 12 amino acids in length, or a variant thereof with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4; and g. an amino acid sequence of SEQ ID NO: 5;

h. a variant of SEQ ID NO: 5 comprising or consisting of an amino acid sequence with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5;

i. a fragment of SEQ ID NO: 5 being more than 180 amino acids in length, such as more than 190, 200, or 210 amino acids in length, or a variant thereof with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5.

In one embodiment, the second peptide comprises a. an amino acid sequence of SEQ ID NO: 3;

b. a variant of SEQ ID NO: 3 comprising or consisting of an amino acid sequence with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3;

c. a fragment of SEQ ID NO: 3 being more than 80 amino acids in length, such as more than 90, 100, or 110 amino acids in length, or a variant thereof with at least 80% sequence identity to the amino acid sequence of SEQ ID NO: 3, more preferably at least 85% or 90% sequence identity to SEQ ID NO: 3, and most preferably at least 95%, 96%, 97%, 98% or 99% identity to SEQ ID NO: 3; and d. an amino acid sequence of SEQ ID NO: 5;

e. a variant of SEQ ID NO: 5 comprising or consisting of an amino acid sequence with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5;

f. a fragment of SEQ ID NO: 5 being more than 180 amino acids in length, such as more than 190, 200, or 210 amino acids in length, or a variant thereof with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5.

In one embodiment, the second peptide comprises a. an amino acid sequence of SEQ ID NO: 4;

b. a variant of SEQ ID NO: 4 comprising or consisting of an amino acid sequence with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4;

c. a fragment of SEQ ID NO: 4 being more than 6 amino acids in length, such as more than 8, 10, or 12 amino acids in length, or a variant thereof with at least 80% sequence identity to the amino acid sequence of SEQ ID NO: 4, more preferably at least 85% or 90% sequence identity to SEQ ID NO: 4, and most preferably at least 95%, 96%, 97%, 98% or 99% identity to SEQ ID NO: 4; and d. an amino acid sequence of SEQ ID NO: 5;

e. a variant of SEQ ID NO: 5 comprising or consisting of an amino acid sequence with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5;

f. a fragment of SEQ ID NO: 5 being more than 180 amino acids in length, such as more than 190, 200, or 210 amino acids in length, or a variant thereof with at least 80% sequence identity to the amino acid sequence of SEQ ID NO: 5, more preferably at least 85% or 90% sequence identity to SEQ ID NO: 5, and most preferably at least 95%, 96%, 97%, 98% or 99% identity to SEQ ID NO: 5.

In one embodiment, the domain A is a translocation domain and the domain C is a cytotoxic domain, such as an ADP-ribosylating domain.

In one embodiment, the second peptide comprises the amino acid sequence KDEL of SEQ ID NO:8 in the C-terminus. In one embodiment, the 5 last amino acids of the second peptide are replaced with the amino acid sequence of SEQ ID NO: 8.

In one embodiment, the second peptide comprises or consists of a. an amino acid sequence of SEQ ID NO: 2;

b. a variant of SEQ ID NO: 2 comprising or consisting of an amino acid sequence with at least 80% sequence identity to the amino acid sequence of SEQ ID NO: 2, more preferably at least 85% or 90% sequence identity to SEQ ID NO: 2, and most preferably at least 95%, 96%, 97%, 98% or 99% identity to SEQ ID NO: 2;

c. a fragment of SEQ ID NO: 2 being more than 300 amino acids in length, such as more than 310, 330, or 340 amino acids in length, or a variant thereof with at least 80% sequence identity to the amino acid sequence of SEQ ID NO: 2, more preferably at least 85% or 90% sequence identity to SEQ ID NO: 2, and most preferably at least 95%, 96%, 97%, 98% or 99% identity to SEQ ID NO: 2.

In one embodiment the second peptide comprises or consists of a variant of SEQ ID NO: 2 comprising or consisting of an amino acid sequence with at least 90% sequence identity to the amino acid sequence of SEQ ID NO: 2. In one embodiment the second peptide comprises or consists of a variant of SEQ ID NO: 2 comprising or consisting of an amino acid sequence with at least 95% sequence identity to the amino acid sequence of SEQ ID NO: 2. In one embodiment the second peptide comprises or consists of a variant of SEQ ID NO: 2 comprising or consisting of an amino acid sequence with at least 96% sequence identity to the amino acid sequence of SEQ ID NO: 2. In one embodiment the second peptide comprises or consists of a variant of SEQ ID NO: 2 comprising or consisting of an amino acid sequence with at least 97% sequence identity to the amino acid sequence of SEQ ID NO: 2. In one embodiment the second peptide comprises or consists of a variant of SEQ ID NO: 2 comprising or consisting of an amino acid sequence with at least 98% sequence identity to the amino acid sequence of SEQ ID NO: 2. In one embodiment the second peptide comprises or consists of a variant of SEQ ID NO: 2 comprising or consisting of an amino acid sequence with at least 99% sequence identity to the amino acid sequence of SEQ ID NO: 2.

In one embodiment the second peptide comprises or consist of a fragment of SEQ ID NO: 2 being more than 300 amino acids in length. In one embodiment the second peptide comprises or consist of a fragment of SEQ ID NO: 2 being more than 310 amino acids in length. In one embodiment the second peptide comprises or consist of a fragment of SEQ ID NO: 2 being more than 330 amino acids in length. In one embodiment the second peptide comprises or consist of a fragment of SEQ ID NO: 2 being more than 340 amino acids in length.

In one embodiment the second peptide comprises or consist of a fragment of SEQ ID NO: 2, or a variant thereof with at least 80% sequence identity to the amino acid sequence of SEQ ID NO: 2. In one embodiment the second peptide comprises or consist of a fragment of SEQ ID NO: 2, or a variant thereof with at least 85% sequence identity to the amino acid sequence of SEQ ID NO: 2. In one embodiment the second peptide comprises or consist of a fragment of SEQ ID NO: 2, or a variant thereof with at least 90% sequence identity to the amino acid sequence of SEQ ID NO: 2. In one embodiment the second peptide comprises or consist of a fragment of SEQ ID NO: 2, or a variant thereof with at least 95% sequence identity to the amino acid sequence of SEQ ID NO: 2. In one embodiment the second peptide comprises or consist of a fragment of SEQ ID NO: 2, or a variant thereof with at least 96% sequence identity to the amino acid sequence of SEQ ID NO: 2. In one embodiment the second peptide comprises or consist of a fragment of SEQ ID NO: 2, or a variant thereof with at least 97% sequence identity to the amino acid sequence of SEQ ID NO: 2. In one embodiment the second peptide comprises or consist of a fragment of SEQ ID NO: 2, or a variant thereof with at least 98% sequence identity to the amino acid sequence of SEQ ID NO: 2. In one embodiment the second peptide comprises or consist of a fragment of SEQ ID NO: 2, or a variant thereof with at least 99% sequence identity to the amino acid sequence of SEQ ID NO: 2.

In one embodiment, the second peptide is less than 400 amino acids in length, for example less than 380, 370, 360, 350 or 345 amino acids in length.

In one embodiment, the second peptide is less than 400 amino acids in length.

In one embodiment, the second peptide is less than 380 amino acids in length.

In one embodiment, the second peptide is less than 370 amino acids in length.

In one embodiment, the second peptide is less than 360 amino acids in length.

In one embodiment, the second peptide is less than 350 amino acids in length.

In one embodiment, the second peptide is less than 345 amino acids in length.

In one embodiment, the fusion protein comprises or consists of a. an amino acid sequence of SEQ ID NO: 6;
  b. a variant of SEQ ID NO: 6 comprising or consisting of an amino acid sequence with at least 80% sequence identity to the amino acid sequence of SEQ ID NO: 6, more preferably at least 85% or 90% sequence identity to SEQ ID NO: 6, and most preferably at least 95%, 96%, 97%, 98% or 99% identity to SEQ ID NO: 6;
  c. a fragment of SEQ ID NO: 6 being more than 360 amino acids in length, such as more than 380, 400, or 420 amino acids in length, or a variant thereof with at least 80% sequence identity to the amino acid sequence of SEQ ID NO: 6, more preferably at least 85% or 90% sequence identity to SEQ ID NO: 6, and most preferably at least 95%, 96%, 97%, 98% or 99% identity to SEQ ID NO: 6.

In one embodiment the fusion protein comprises or consists of a variant of SEQ ID NO: 6 comprising or consisting of an amino acid sequence with at least 90% sequence identity to the amino acid sequence of SEQ ID NO: 6. In one embodiment the fusion protein comprises or consists of a variant of SEQ ID NO: 6 comprising or consisting of an amino acid sequence with at least 95% sequence identity to the amino acid sequence of SEQ ID NO: 6. In one embodiment the fusion protein comprises or consists of a variant of SEQ ID NO: 6 comprising or consisting of an amino acid sequence with at least 96% sequence identity to the amino acid sequence of SEQ ID NO: 6. In one embodiment the fusion protein comprises or consists of a variant of SEQ ID NO: 6 comprising or consisting of an amino acid sequence with at least 97% sequence identity to the amino acid sequence of SEQ ID NO: 6. In one embodiment the fusion protein comprises or consists of a variant of SEQ ID NO: 6 comprising or consisting of an amino acid sequence with at least 98% sequence identity to the amino acid sequence of SEQ ID NO: 6. In one embodiment the fusion protein comprises or consists of a variant of SEQ ID NO: 6 comprising or consisting of an amino acid sequence with at least 99% sequence identity to the amino acid sequence of SEQ ID NO: 6.

In one embodiment the fusion protein comprises or consist of a fragment of SEQ ID NO: 6 being more than 360 amino acids in length. In one embodiment the fusion protein comprises or consist of a fragment of SEQ ID NO: 6 being more than 380 amino acids in length. In one embodiment the fusion protein comprises or consist of a fragment of SEQ ID NO: 6 being more than 400 amino acids in length. In one embodiment the fusion protein comprises or consist of a fragment of SEQ ID NO: 6 being more than 420 amino acids in length.

In one embodiment the fusion protein comprises or consist of a fragment of SEQ ID NO: 6, or a variant thereof with at least 80% sequence identity to the amino acid sequence of SEQ ID NO: 6. In one embodiment the fusion protein comprises or consist of a fragment of SEQ ID NO: 6, or a variant thereof with at least 85% sequence identity to the amino acid sequence of SEQ ID NO: 6. In one embodiment the fusion protein comprises or consist of a fragment of SEQ ID NO: 6, or a variant thereof with at least 90% sequence identity to the amino acid sequence of SEQ ID NO: 6. In one embodiment the fusion protein comprises or consist of a fragment of SEQ ID NO: 6, or a variant thereof with at least 95% sequence identity to the amino acid sequence of SEQ ID NO: 6. In one embodiment the fusion protein comprises or consist of a fragment of SEQ ID NO: 6, or a variant thereof with at least 96% sequence identity to the amino acid sequence of SEQ ID NO: 6. In one embodiment the fusion protein comprises or consist of a fragment of SEQ ID NO: 6, or a variant thereof with at least 97% sequence identity to the amino acid sequence of SEQ ID NO: 6. In one embodiment the fusion protein comprises or consist of a fragment of SEQ ID NO: 6, or a variant thereof with at least 98% sequence identity to the amino acid sequence of SEQ ID NO: 6. In one embodiment the fusion protein comprises or consist of a fragment of SEQ ID NO: 6, or a variant thereof with at least 99% sequence identity to the amino acid sequence of SEQ ID NO: 6.

In one embodiment, the fusion protein is less than 500 amino acids in length, for example less than 490, 480, 470, 460, 450, 440, 430, 425 or less amino acids in length.

In one embodiment, the fusion protein is less than 500 amino acids in length. In one embodiment, the fusion protein is less than 490 amino acids in length. In one embodiment, the fusion protein is less than 480 amino acids in length. In one embodiment, the fusion protein is less than 470 amino acids in length. In one embodiment, the fusion protein is less than 460 amino acids in length. In one embodiment, the fusion protein is less than 450 amino acids in length. In one embodiment, the fusion protein is less than 440 amino acids in length. In one embodiment, the fusion protein is less than 430 amino acids in length. In one embodiment, the fusion protein is less than 420 amino acids in length.

In one embodiment, the fusion protein kills cells infected by a pathogen, such as cells latently infected by a pathogen.

In one embodiment, the pathogen is a virus such as DNA virus such as a herpesvirus, such as cytomegalovirus, or a RNA virus.

In one embodiment, the fusion protein induces cell death of cells expressing the receptor.

In one embodiment, the cell death is selected from the group consisting of apoptosis, necrosis, autophagic cell death and mitosis associated cell death. The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function.

In one embodiment, the fusion protein induces a direct or indirect effect on a pathogen resulting in inhibition of pathogen growth, replication, genome stability, maturation, packaging, latency, reactivation, dissemination and/or immune inhibition.

In one embodiment, the fusion protein selectively kills cells that express a pathogen encoded receptor.

In one embodiment, the fusion protein kills cells that express US28.

In one embodiment, the fusion protein has an IC50 value of less than 10 nM, such as less than 5 nM, for example less than 1 nM, such as less than 0.5 nM, for example less than 0.1 nM or less than 0,001 nM for a receptor encoded by a virus such as US28.

In one embodiment, the fusion protein has increased potency against cells expressing a receptor encoded by a virus, such as US28, as compared to the potency against cells expressing an endogenous receptor or human encoded receptor, such as CX3CR1, such as at least 100-fold increased potency, such as at least 300-fold increased potency, such as at least 400-fold increased potency, such as at least 500-fold increased potency. In one embodiment, the fusion protein has increased potency against cells expressing US28 as compared to the potency against cells expressing CX3CR1, such as at least 100-fold increased potency. In one embodiment, the fusion protein has increased potency against cells expressing US28 as compared to the potency against cells expressing CX3CR1, such as at least 300-fold increased potency In one embodiment, the fusion protein has increased potency against cells expressing US28 as compared to the potency against cells expressing CX3CR1, such as at least 400-fold increased potency. In one embodiment, the fusion protein has increased potency against cells expressing US28 as compared to the potency against cells expressing CX3CR1, such as at least 500-fold increased potency.

In one embodiment, the fusion protein has increased affinity for a receptor encoded by a virus such as US28 as compared to the affinity for an endogenous receptor or human encoded receptor such as CX3CR1, such as at least 50-fold increased affinity, such as at least 100-fold increased affinity. In one embodiment, the fusion protein has increased affinity for US28 as compared to the affinity for CX3CR1, such as at least 100-fold increased affinity.

In one embodiment, the selectivity ratio US28/CX3CR1 of the fusion protein of the present invention is at least 750, such as at least 800, such as at least 850, such as at least 900. In one embodiment, the selectivity ratio US28/CX3CR1 of the fusion protein of the present invention is at least 880. In one embodiment, the selectivity ratio US28/CX3CR1 of the fusion protein of the present invention is at least 750. In one embodiment, the selectivity ratio US28/CX3CR1 of the fusion protein of the present invention is at least 800. In one embodiment, the selectivity ratio US28/CX3CR1 of the fusion protein of the present invention is at least 850. In one embodiment, the selectivity ratio US28/CX3CR1 of the fusion protein of the present invention is at least 900.

Nucleic Acid

In one aspect, the present invention provides an isolated nucleic acid molecule encoding a fusion protein as described herein.

By "nucleic acid molecule" we include DNA (e.g. genomic DNA or complementary DNA) and mRNA molecules, which may be single- or double-stranded. By "isolated" we mean that the nucleic acid molecule is not located or otherwise provided within a cell.

Vector

In one aspect, the present invention provides a vector comprising a nucleic acid molecule as described herein.

In one embodiment, the vector is an expression vector.

Host Cell

In one aspect, the present invention provides a recombinant host cell comprising a nucleic acid molecule or a vector as described herein.

In one embodiment, the host cell is a bacterial cell, a yeast cell, a mammalian cell such as a human cell or an insect cell.

Pharmaceutical Composition

In one aspect, the present invention provides a pharmaceutical composition comprising a fusion protein, a nucleic acid, a vector or a recombinant host cell as described herein and a pharmaceutically acceptable carrier, diluent and/or excipient.

In one embodiment, the pharmaceutical composition further comprises one or more agents. In one embodiment, the agent is selected from the group consisting of immunosuppressive agents, anti-viral agents and immunotherapy.

In one embodiment, the anti-viral agent is selected from the group consisting of valganciclovir, ganciclovir, cidofovir, leflunomide, prevymis, maribavir and brincidofovir.

In one embodiment, the immunotherapy is cell-based therapy. In one embodiment, the immunotherapy is T cell therapy.

Diseases

In one aspect, the present invention provides a fusion protein, a nucleic acid, a vector, a recombinant host cell or a pharmaceutical composition as described herein for use as a medicament.

In another aspect, the present invention provides a fusion protein, a nucleic acid, a vector, a recombinant host cell or a pharmaceutical composition as described herein for use in the prevention or treatment of an infection caused by a pathogen and/or a pathogen associated disorder.

In one embodiment, the pathogen is a bacteria or a virus. In one embodiment, the virus is a DNA virus, such as a herpesvirus, such as cytomegalovirus, or a RNA virus.

In one aspect, the present invention provides a fusion protein, a nucleic acid, a vector, a recombinant host cell or a pharmaceutical composition as described herein for use in the prevention or treatment of CMV infections and/or CMV-associated disorders.

In one embodiment, the CMV infection is a latent and/or lytic CMV infection.

In one embodiment, the CMV infection can be detected in:
  i) a tissue selected from one or more of the group consisting of retina, cornea, heart, liver, kidney, lung, gastro-intestinal tissue, thymus, spleen, skin and muscle, and/or
  ii) a body fluid selected from one or more of the group consisting of saliva, blood, urine, semen and breast milk.

In one embodiment, the CMV infection is an infection in an immuno-compromised patient selected from the group consisting of HIV-patients, neonates and immunosuppressive patients, bone marrow transplant patients, solid organ transplant patients, immune therapy patients, cancer patients, intensive care patients, trauma patients, stem cell patients, gene therapy patients, cell therapy patients, geriatric patients and multimorbid patients.

In one embodiment, the CMV infection is an infection in a patient suffering from a coronary disease and/or a vascular disease.

In one embodiment, the fusion protein, the nucleic acid, the vector, the host cell or the composition is administered intravenously, intratumorously, intraperitoneally, intrathecally and/or intralymphatically.

In one embodiment, the fusion protein, the nucleic acid, the vector, the host cell or the composition is administered one or more times to the individual.

In one embodiment, the individual is a human.

In one embodiment, the human is an immunocompromised patient. By immunocompromised patient, we refer to a patient not having the ability to respond normally to an infection due to an impaired or weakened immune system. For example, an immunocompromised patient may be diagnosed with a disease that affect the immune system such as diabetes and HIV. An immunocompromised patient may have a suppressed immune response following treatment such as chemotherapy.

In one embodiment, the human is a child. In one embodiment, the human is an adult.

In one embodiment, the human is in need of a solid organ transplantation and/or a hematopoietic stem cell transplantation. Hematopoietic stem cell transplantation is the transplantation of multipotent hematopoietic stem cells, usually derived from one marrow, peripheral blood or umbilical cord blood. The transplantation may be autologous (stem cells are isolated from the same patient) or allogeneic (stem cells are isolated from a different patient).

In one embodiment, the CMV-associated disorder is selected from the group consisting of cytomegaloviral pneumonitis, cytomegaloviral hepatitis, cytomegaloviral pancreatitis, cytomegaloviral mononucleosis, CMV polyradiculomyelopathy, cytomegalic inclusion body disease, cytomegalovirus colitis, cytomegalovirus esophagitis, cytomegalovirus retinitis, Guillain-Barre syndrome, mucoepidermoid carcinoma and ulcerative colitis, graft versus host disease (GVHD), solid organ transplant graft versus host disease (SOT-GVHD).

In one aspect, the present invention provides a fusion protein, a nucleic acid, a vector, a host cell or a pharmaceutical composition as described herein for use in the manufacture of a medicament for the prevention or treatment of an infection caused by a pathogen and/or pathogen associated disorders, such as for the prevention or treatment of CMV infections and/or CMV-associated disorders.

In another aspect, the present invention provides an ex vivo use of a fusion protein or a pharmaceutical composition as described herein for treatment of solid organs for transplantation and/or hematopoietic stem cells for transplantation.

The terms "treating," "treatment," and "therapy" as used herein refer to curative therapy, prophylactic therapy, ameliorative and palliative therapy. Preferably, the treatment is curative.

Method of Treatment

In one aspect, the present invention provides a method of treating or preventing infection caused by a pathogen such as CMV infections in an individual in need thereof, the method comprising administering a therapeutically effective amount of a fusion protein, a nucleic acid, a vector, a recombinant host cell or a pharmaceutical composition as described herein to the individual.

An "effective amount" or "therapeutically effective amount" of a compound is that amount of compound which is sufficient to provide a beneficial effect to the subject to which the compound is administered. The phrase "therapeutically effective amount," as used herein, may refer to an amount of a fusion protein that is sufficient or effective to treat (delay or prevent the onset of, prevent the progression of, inhibit, decrease or reverse) an infection.

Method for Producing

In one aspect, the present invention provides a method for producing a fusion protein as described herein, the method comprising culturing a host cell as defined herein under conditions which permit expression of the encoded fusion protein.

```
Sequences
(exemplary first peptide)
                                SEQ ID NO: 1
QHHGVTKCNITCSKMTSKIPVALLIHYQQNQASCG

KRAIILETRQHRLFCADPKEQWVKDAMQHLDRQAA

ALTRNG (exemplary second peptide)
                                SEQ ID NO: 2
GGSLAALTAHQACHLPLETFTRHRQRRGWEQLEQC

GYPVQRLVALYLAARLSWNQVDQVIRNALASPGSG

GDLGEAIREQPEQARLALTLAAAESERFVRQGTGN

DEAGAASGPADSGDALLERNYPTGAEFLGDGGDIS

FSTRGTQNWTVERLLQAHRQLEERGYVFVGYHGTF

LEAAQSIVFGGVRARSQDLDAIWRGFYIAGDPALA

YGYAQDQEPDARGRIRNGALLRVYVPRSSLPGFYR

TGLTLAAPEAAGEVERLIGHPLPLRLDAITGPEEE

GGRLETILGWPLAERTWIPSAIPTDPRNVGGDLDP

SSIPDKEQAISALPDYASQPGKPP (Domain A of Exotoxin A)
                                SEQ ID NO: 3
GGSLAALTAHQACHLPLETFTRHRQRRGWEQLEQC

GYPVQRLVALYLAARLSWNQVDQVIRNALASPGSG

GDLGEAIREQPEQARLALTLAAAESERFVRQGTGN

DEAGAAS (Domain B of Exotoxin A)
                                SEQ ID NO: 4
GPADSGDALLERNYP (Domain C of Exotoxin A)
                                SEQ ID NO: 5
TGAEFLGDGGDISFSTRGTQNWTVERLLQAHRQLE

ERGYVFVGYHGTFLEAAQSIVFGGVRARSQDLDAI

WRGFYIAGDPALAYGYAQDQEPDARGRIRNGALLR

VYVPRSSLPGFYRTGLTLAAPEAAGEVERLIGHPL

PLRLDAITGPEEEGGRLETILGWPLAERTWIPSAI

PTDPRNVGGDLDPSSIPDKEQAISALPDYASQPGK

PP (SYN002)
                                SEQ ID NO: 6
MQHHGVTKCNITCSKMTSKIPVALLIHYQQNQASC

GKRAIILETRQHRLACADPKEQWVKDAMQHLDRQA

AALTRNGGGSLAALTAHQACHLPLETFTRHRQRRG

WEQLEQCGYPVQRLVALYLAARLSWNQVDQVIRNA

LASPGSGGDLGEAIREQPEQARLALTLAAAESERF

VRQGTGNDEAGAASGPADSGDALLERNYPTGAEFL

GDGGDISFSTRGTQNWTVERLLQAHRQLEERGYVF
```

19

-continued

VGYHGTFLEAAQSIVFGGVRARSQDLDAIWRGFYI

AGDPALAYGYAQDQEPDARGRIRNGALLRVYVPRS

SLPGFYRTGLTLAAPEAAGEVERLIGHPLPLRLDA

ITGPEEEGGRLETILGWPLAERTWIPSAIPTDPRN

VGGDLDPSSIPDKEQAISALPDYASQPGKPPKDEL (human CX3CL1)

SEQ ID NO: 7

MAPISLSWLLRLATFCHLTVLLAGQHHGVTKCNIT

CSKMTSKIPVALLIHYQQNQASCGKRAIILETRQH

RLFCADPKEQWVKDAMQHLDRQAAALTRNGGTFEK

QIGEVKPRTTPAAGGMDESVVLEPEATGESSSLEP

TPSSQEAQRALGTSPELPTGVTGSSGTRLPPTPKA

QDGGPVGTELFRVPPVSTAATWQSSAPHQPGPSLW

AEAKTSEAPSTQDPSTQASTASSPAPEENAPSEGQ

RVWGQGQSPRPENSLEREEMGPVPAHTDAFQDWGP

GSMAHVSWPVSSEGTPSREPVASGSWTPKAEEPIH

ATMDPQRLGVLITPVPDAQAATRRQAVGLLAFLGL

LFCLGVAMFTYQSLQGCPRKMAGEMAEGLRYIPRS

CGSNSYVLVPV (Sequence securing binding to KDEL-
receptor for retrograde transport
inside cell)

SEQ ID NO: 8

KDEL (full length Exotoxin A)

SEQ ID NO: 9

MHLTPHWIPLVASLGLLAGGSFASAAEEEAFDLWNE

CAKACVLDLKDGVRSSRMSVDPAIADTNGQGVLHY

SMVLEGGNDALKLAIDNALSITSDGLTIRLEGGVE

PNKPVRYSYTRQARGSWSLNWLVPIGHEKPSNIKV

FIHELNAGNQLSHMSPIYTIEMGDELLAKLARDAT

FFVRAHESNEMQPTLAISHAGVSWMAQAQPRREKR

WSEWASGKVLCLLDPLDGVYNYLAQQRCNLDDTWE

GKIYRVLAGNPAKHDLDIKPTVISHRLHFPEGGSL

AALTAHQACHLPLETFTRHRQPRGWEQLEQCGYPV

QRLVALYLAARLSWNQVDQVIRNALASPGSGGDLG

EAIREQPEQARLALTLAAAESERFVRQGTGNDEAG

AASADWSLTCPVAAGECAGPADSGDALLERNYPTG

AEFLGDGGDISFSTRGTQNWTVERLLQAHRQLEER

GYVFVGYHGTFLEAAQSIVFGGVRARSQDLDAIWR

GFYIAGDPALAYGYAQDQEPDARGRIRNGALLRVY

VPRSSLPGFYRTGLTLAAPEAAGEVERLIGHPLPL

20

-continued

RLDAITGPEEEGGRLETILGWPLAERTVVIPSAIP

TDPRNVGGDLDPSSIPDKEQAISALPDYASQPGKP

PREDLK (US28)

SEQ ID NO: 10

MTPTTTTAELTTEFDYDEAATPCVFTDVLNQSKPV

TLFLYGWFLFGSIGNFLVIFTITWRRRIQCSGDVY

FINLAAADLLFVCTLPLWMQYLLDHNSLASVPCTL

LTACFYVAMFASLCFITEIALDRYYAIVYMRYRPV

KQACLFSIFWWIFAVIIAIPHFMVVTKKDNQCMTD

YDYLEVSYPIILNVELMLGAFVIPLSVISYCYYRI

SRIVAVSQSRHKGRIVRVLIAVVLVFIIFWLPYHL

TLFVDTLKLLKWISSSCEFERSLKRALILTESLAF

CHCCLNPLLYVFVGTKFRQELHCLLAEFRQRLFSR

DVSWYHSMSFSRRSSPSRRETSSDTLSDEVCRVSQ

IIP (SYN000)

SEQ ID NO: 11

MQHHGVTKCNITCSKMTSKIPVALLIHYQQNQASC

GKRAIILETRQHRLFCADPKEQWVKDAMQHLDRQA

AALTRNRQPRGWEQLEQSGYPVQRLVALYLAARLS

WNQVDQVIRNALASPGSGGDLGEAIREQPEQARLA

LTLAAAESERFVRQGTGNDEAGAASGPADSGDALL

ERNYPTGAEFLGDGGDISFSTRGTQNWTVERLLQA

HRQLEERGYVFVGYHGTFLEAAQSIVFGGVRARSQ

DLDAIWRGFYIAGDPALAYGYAQDQEPDARGRIRN

GALLRVYVPRSSLPGFYRTGLTLAAPEAAGEVERL

IGHPLPLRLDAITGPEEEGGRLETILGWPLAERTV

VIPSAIPTDPRNVGGDLDPSSIPDKEQAISALPDY

ASQPGKPPKDEL (SYN001)

SEQ ID NO: 12

MQHHGVTKCNITCSKMTSKIPVALLIHYQQNQASC

GKRAIILETRQHRLACADPKEQWVKDAMQHLDRQA

AALTRNRQPRGWEQLEQSGYPVQRLVALYLAARLS

WNQVDQVIRNALASPGSGGDLGEAIREQPEQARLA

LTLAAAESERFVRQGTGNDEAGAASGPADSGDALL

ERNYPTGAEFLGDGGDISFSTRGTQNWTVERLLQA

HRQLEERGYVFVGYHGTFLEAAQSIVFGGVRARSQ

DLDAIWRGFYIAGDPALAYGYAQDQEPDARGRIRN

GALLRVYVPRSSLPGFYRTGLTLAAPEAAGEVERL

IGHPLPLRLDAITGPEEEGGRLETILGWPLAERTV

-continued

VIPSAIPTDPRNVGGDLDPSSIP

DKEQAISALPDYASQPGKPPKDE (SYN014)

SEQ ID NO: 13

MQHHGVTKCNITCSKMTSKIPVALLIHYQQNQASC

GKRAIILETRQHRLFCADPKEQWVKDAMQHLDRQA

AALTRNGGGSLAALTAHQACHLPLETFTRHRQRRG

WEQLEQCGYPVQRLVALYLAARLSWNQVDQVIRNA

LASPGSGGDLGEAIREQPEQARLALTLAAAESERF

VRQGTGNDEAGAASGPADSGDALLERNYPTGAEFL

GDGGDISFSTRGTQNWTVERLLQAHRQLEERGYVF

VGYHGTFLEAAQSIVFGGVRARSQDLDAIWRGFYI

AGDPALAYGYAQDQEPDARGRIRNGALLRVYVPRS

SLPGFYRTGLTLAAPEAAGEVERLIGHPLPLRLDA

ITGPEEEGGRLETILGWPLAERTVVIPSAIPTDPR

NVGGDLDPSSIPDKEQAISALPDYASQPGKPPKDE

L (SYN016)

SEQ ID NO: 14

MQHHGVTKCNITCSKMTSKIPVALLIHYQQNQASC

GKRAIILETRQHRLACADPKEQWVKDAMQHLDRQA

AALTRNGGGSLAALTAHQACHLPLETFTRHRQPRG

WEQLEQCGYPVQRLVALYLAARLSWNQVDQVIRNA

LASPGSGGDLGEAIREQPEQARLALTLAAAESERF

VRQGTGNDEAGAASGPADSGDALLERNYPTGAEFL

GDGGDISFSTRGTQNWTVERLLQAHRQLEERGYVF

VGYHGTFLEAAQSIVFGGVRARSQDLDAIWRGFYI

AGDPALAYGYAQDQEPDARGRIRNGALLRVYVPRS

SLPGFYRTGLTLAAPEAAGEVERLIGHPLPLRLDA

ITGPEEEGGRLETILGWPLAERTWIPSAIPTDPRN

VGGDLDPSSIPDKEQAISALPDYASQPGKPPKDEL (SYN017)

SEQ ID NO: 15

MQHHGVTKCNITCSKMTSKIPVALLIHYQQNQASC

GKRAIILETRQHRLFCADPKEQWVKDAMQHLDRQA

AALTRNGGGSLAALTAHQACHLPLETFTRHRQPRG

WEQLEQCGYPVQRLVALYLAARLSWNQVDQVIRNA

LASPGSGGDLGEAIREQPEQARLALTLAAAESERF

VRQGTGNDEAGAASGPADSGDALLERNYPTGAEFL

GDGGDISFSTRGTQNWTVERLLQAHRQLEERGYVF

VGYHGTFLEAAQSIVFGGVRARSQDLDAIWRGFYI

AGDPALAYGYAQDQEPDARGRIRNGALLRVYVPRS

SLPGFYRTGLTLAAPEAAGEVERLIGHPLPLRLDA

22

-continued

ITGPEEEGGRLETILGWPLAERTVVIPSAIPTDPR

NVGGDLDPSSIPDKEQAISALPDYASQPGKPPKDE

L

Items

1. A fusion protein comprising:
   a) a first peptide which binds to at least one receptor expressed on a cell; and
   b) a second peptide comprising a cleavage site having an amino acid sequence ArgX1X2Arg,
   wherein X2 is Arg or Lys, and wherein the second peptide comprises a toxin.

2. The fusion protein according to item 1, wherein the fusion protein is an immunotoxin.

3. The fusion protein according to any one of the preceding items, wherein the cleavage site comprises or consists of the amino acid sequence ArgGlnArgArg.

4. The fusion protein according to any one of the preceding items, wherein the first peptide binds to at least two different receptors expressed on a cell.

5. The fusion protein according to any one of the preceding items, wherein one receptor binding the first peptide is a receptor encoded by a pathogen and a further receptor binding the first peptide is a human encoded receptor and/or endogenous receptor for the first peptide or a variant thereof.

6. The fusion protein according to any one of the preceding items, wherein the receptor is a G-protein coupled receptor (GPCR), such as US28 of SEQ ID NO: 10.

7. The fusion protein according to any one of the preceding items, wherein the second peptide comprises a toxin selected from the group consisting of *Pseudomonas* exotoxin A, gelonin, bouganin, saporin, ricin, ricin A chain, bryodin, restrictocin, diphteria toxin, diphteria toxin A chain and variants and fragments thereof.

8. The fusion protein according to any one of the preceding items, wherein the receptor is internalized upon binding to the first peptide.

9. The fusion protein according to any one of the preceding items, wherein the receptor is constitutively internalized.

10. The fusion protein according to any one of the preceding items, wherein the first peptide comprises or consists of
    a. an amino acid sequence of SEQ ID NO: 1;
    b. a variant of SEQ ID NO: 1 comprising or consisting of an amino acid sequence with at least 80% sequence identity to the amino acid sequence of SEQ ID NO: 1, more preferably at least 85% or 90% sequence identity to SEQ ID NO: 1, and most preferably at least 95%, 96%, 97%, 98% or 99% identity to SEQ ID NO: 1;
    c. a fragment of SEQ ID NO: 1 being more than 50 amino acids in length, such as more than 60, 70, or 75 amino acids in length, or a variant thereof with at least 80% sequence identity to the amino acid sequence of SEQ ID NO: 1, more preferably at least 85% or 90% sequence identity to SEQ ID NO: 1, and most preferably at least 95%, 96%, 97%, 98% or 99% identity to SEQ ID NO: 1.

11. The fusion protein according to any one of the preceding items, wherein the second peptide comprises or consists of
    a. an amino acid sequence of SEQ ID NO: 2;
    b. a variant of SEQ ID NO: 2 comprising or consisting of an amino acid sequence with at least 80% sequence identity to the amino acid sequence of SEQ ID NO: 2, more preferably at least 85% or 90% sequence identity to SEQ ID NO: 2, and most preferably at least 95%, 96%, 97%, 98% or 99% identity to SEQ ID NO: 2;
    c. a fragment of SEQ ID NO: 2 being more than 300 amino acids in length, such as more than 310, 330, or 340 amino acids in length, or a variant thereof with at least 80% sequence identity to the amino acid sequence of SEQ ID NO: 2, more preferably at least 85% or 90% sequence identity to SEQ ID NO: 2, and most preferably at least 95%, 96%, 97%, 98% or 99% identity to SEQ ID NO: 2.

12. The fusion protein according to any one of the preceding items, wherein the fusion protein comprises or consists of
    a. an amino acid sequence of SEQ ID NO: 6;
    b. a variant of SEQ ID NO: 6 comprising or consisting of an amino acid sequence with at least 80% sequence identity to the amino acid sequence of SEQ ID NO: 6, more preferably at least 85% or 90% sequence identity to SEQ ID NO: 6, and most preferably at least 95%, 96%, 97%, 98% or 99% identity to SEQ ID NO: 6;
    c. a fragment of SEQ ID NO: 6 being more than 360 amino acids in length, such as more than 380, 400, or 420 amino acids in length, or a variant thereof with at least 80% sequence identity to the amino acid sequence of SEQ ID NO: 6, more preferably at least 85% or 90% sequence identity to SEQ ID NO: 6, and most preferably at least 95%, 96%, 97%, 98% or 99% identity to SEQ ID NO: 6.

13. The fusion protein according to any one of the preceding items, wherein the fusion protein kills cells infected by a pathogen, such as cells latently infected by a pathogen.

14. The fusion protein according to any one of the preceding items, wherein the fusion protein has increased potency against cells expressing a receptor encoded by a virus such as US28 as compared to the potency against cells expressing an endogenous receptor or human encoded receptor such as CX3CR1, such as at least 300-fold increased potency, such as at least 400-fold increased potency, such as at least 500-fold increased potency, such as at least 700-fold increased potency.

15. A fusion protein according to any one of items 1 to 14 for use in the prevention or treatment of an infection caused by a pathogen and/or pathogen associated disorders.

16. A fusion protein according to any one of items 1 to 14 for use in the prevention or treatment of CMV infections and/or CMV-associated disorders.

EXAMPLES

Example 1: Mutation in the First Peptide of the Fusion Protein SYNx Leads to Selectivity in Cell Killing

Materials and Methods

Inducible US28- or CX3CR1-Expressing HEK293 Cells

For the binding and cell killing assays, cells were constructed as described in Hjortø G M et al., 2013. Briefly, stable and inducible clones of HA-CX3CR1- and HA-US28-expressing cells were generated by co-transfecting Flp-In T-Rex-293 cells with the Flp-recombinase expression vector, pOG44 and either of the pcDNA5/FRT/TO receptor constructs. This targeted cloning at the FRT site brings the receptor gene under the control of the Tetracycline repressor/operator system. The expression of the receptors was confirmed by Western blotting. For cell culturing a cell cells were grown in a humidified incubator (37° C., 5% CO2) in 1×DMEM (with 9% (v/v) FBS, 180 U/mL Penicillin and 45 μg/mL Streptomycin, 13.5 μg/mL Blasticidin and 1.32 mg/mL Hygromycin B.

Cell Killing Assay

80 μL of 20 μg/mL Poly-D-Lysine (PDL) in 1×PBS was added to each well of a white 96-well plate and incubated for 30 min at room temperature. The inducible US28- or CX3CR1-expressing HEK293 cells were washed in 10 mL of 1×PBS and released with 2 mL of 0.05% (w/v) Trypsin-EDTA for 2 min. The cells were resuspended in 10 mL of growth medium (1×DMEM, 9% (v/v) FBS, 180 U/mL Penicillin and 45 μg/mL Streptomycin) and the cell density was then determined. The PDL-solution was aspirated from the plate and each well was washed with 100 μL 1×PBS. After aspiration of the wash buffer, the 96-well plate was seeded with 2,000 to 10,000 cells/well in 100 μL and placed in a 002-incubator (37° C., 10% CO2) overnight.

For receptor expression, 10 μL of Tetracycline, 1.375 μg/mL US28 and 5.5 μg/mL CX3CR1)) in growth medium without selection was added to each well in the plate, which was placed back in the 002-incubator (37° C., 10% CO2) overnight.

A fusion toxin protein aliquot was thawed on ice and used to make a dilution series in 1 mM Acetic acid and 5 g/L BSA. The receptor expression growth media was aspirated and replaced with 100 μL of fresh growth media. 5 μL of the fusion toxin protein dilution series was added to each well and 5 μL of 1 g/L Cycloheximide was added as a positive control to one well. The plate was placed back in the 002-incubator (37° C., 10% CO2) overnight.

A 1:10 dilution of AlamarBlue in assay growth medium was prepared. The solution was covered with tinfoil and heated for 10 min. in a 37° C. water bath and then filtered through a 0.2 μm filter. The well solutions were aspirated and 100 μL of the AlamarBlue solution was added to each well and the plate was placed back in the 002-incubator (37° C., 10% CO2) for 4 hours. Fluorescence data was collected on a FlexStation 3 using excitation at 540 nm and emission at 585 nm.

Results

Cell killing efficiency of SYNx was determined using tetracycline-induced HEK 293 cells expressing either a receptor encoded by a virus such as US28 or an endogenous receptor such as CX3CR1 together with non-induced cells with no receptor expression (negative controls). The data were normalized to the maximum number of living cells. Substituting a single amino acid in the first peptide (here chemokine part) of SYNx leads to selectivity towards the virus encoded receptor US28 as shown in FIG. 2. Both constructs bind with similar selectivity to US28 (FIG. 2A), while SYN001, which has a single mutation (F49A, corresponding to F73A using precursor numbering) in the first peptide (receptor binding part) of the protein, is less selective towards the endogenous receptor, here CXC3R1 (FIG. 2B).

Conclusion

The single amino acid F49A substitution in the first peptide (e.g a chemokine part) of the fusion protein construct induces selectivity of the fusion protein (SYNx) towards the virus encoded receptor US28.

Example 2: Increased Potency Obtained by Adding a Furin Cleavage Site Through the Full Length Translocation Domain of Exotoxin A

Materials and Methods

See Example 1

Results

Cell killing efficiency of SYNx was determined using tetracycline-induced HEK 293 cells expressing either the virus encoded receptor US28 or the endogenous receptor CX3CR1 together with non-induced cells with no receptor expression (negative controls). The data were normalized to the maximum number of living cells. Adding a furin cleavage site, such as the full length translocation domain, to the SYN001 construct, yielding SYN016, increases the potency on both the endogenous/human CX3CR1- and the pathogen encoded US28-receptor expressing cells as shown in FIG. 3 and table 1.

Conclusion

Domain II of Exotoxin A has been identified as the translocation domain responsible for the transfer of the catalytic domain, domain III, from an endocytic vesicle into the cytosol (Hwang J et. al., 1987; Siegal) C B et al., 1989). Adding a translocation domain comprising a furin cleavage site, such as the domain II of Exotoxin A, to SYN001, yielding SYN016, resulted in a fusion protein construct with increased potency on both the endogenous receptor CX3CR1 and the virus encoded receptor US28.

1×MES running buffer containing 2 mM DTT according to the manufactures protocol. The gel was run at 125 V constant voltage for 75 min. The gel was stained according to the SimplyBlue™ SafeStain Manual (Novex).

Results

Purified SYNx constructs were treated with purified human Furin in vitro to determine the cleavage efficiency of the different SYNx constructs by Furin. Other cleavage mechanisms than by Furin may possibly take place. The results were analysed by SDS-PAGE. Addition of a full translocation domain, such as in this case a full ExoA translocation domain, to SYN000 or SYN001, yielding SYN017 and SYN016 respectively, improves in vitro cleavage by Furin. Optimization of the Furin cleavage site in SYN017 and SYN016, yielding SYN014 and SYN002 respectively, does not appear to improve in vitro cleavage by Furin further. as shown in FIG. 4.

Purified SYN002 was treated with purified human Furin in vitro at different pH values to determine the cleavage efficiency and the results were analysed by SDS-PAGE. SYN002 is cleaved by Furin over a wide pH range as shown in FIG. 5.

Conclusion

Adding an optimized cleavage site (in this case Arg-GlnArgArg), to the SYNx constructs (here the SYN002-construct also comprising the translocation domain) does not yield an improvement in the in vitro cleavage by Furin, compared to a construct with the native sequence (ArgGln-ProArg) as in SYN016. SYN002 could be cleaved in vitro over a broad pH range, suggesting that cleavage by Furin could occur at any cellular location and not only in endosomes.

TABLE 1

| | IC50 values of different fusion protein constructs | | | | | | | |
| --- | --- | --- | --- | --- | --- | --- | --- | --- |
| | SYN001 US28 | SYN001 CX3CR1 | SYN016 US28 | SYN016 CX3CR1 | SYN016 US28 | SYN016 CX3CR1 | SYN002 US28 | SYN002 CX3CR1 |
| Log IC50 | −10.68 +/− 0.10 | −7.82 +/− 0.06 | −12.27 +/− 0.08 | −9.66 +/− 0.09 | −12.27 +/− 0.08 | −9.66 +/− 0.09 | −11.90 +/− 0.08 | −8.95 +/− 0.06 |
| Selectivity Ratio US28/CX3CR1 | 718 | | 406 | | 406 | | 889 | |

Example 3: In Vitro Cleavage of SYNx by Human Furin

Materials and Methods

In Vitro Cleavage of SYNx by Human Furin

The purified SYNx construct was thawed on the lab bench. When thawed, the sample was then spun down. The concentration of the sample was measured and a digest was set up with 20 μM SYNx in 50 μL in a new tube in 1×PBS containing 5 mM CaCl$_2$). 5 μg was removed for SDS-PAGE analysis. 1 μL of human Furin (NEB, 2 units/μL) was added to the mixture and was placed in a water bath at 37° C. After 1.5 hours 5 μg of SYNx was removed for SDS-PAGE analysis. The pH of the reaction mixture is adjusted with either 1 M HCL or 1 M NaOH prior to addition of SYNx.

Reduced SDS-PAGE Analysis

Samples were prepared and along with a protein marker standard analysed on a NuPAGE Bis-Tris 4-12% gel with

Example 4: Cell Killing Selectivity Between Endogenous and Virus Encoded Receptor-Expressing Cells is Also Enhanced and Mediated by the Optimized Cleavage Site

Materials and Methods

See Example 1

Results

Cell killing efficiency of SYNx was determined using tetracycline-induced HEK 293 cells expressing either US28 or CX3CR1 together with non-induced cells with no receptor expression (negative controls). The data was normalized to the maximum number of living cells.

When introducing an optimized cleavage site ArgX1X2Arg into the second peptide, in this particular case the optimized cleavage site ArgGlnArgArg into SYN016 to give SYN002, a surprising increase in selectivity is obtained. For SYN002 on cells expressing a virus encoded receptor such as US28 in the cell killing potency is approximately maintained compared to SYN016 having an cleavage site ArgGlnProArg (thus X2=Pro) (FIG. 6A, table 1). However, the potency on cells expressing an endogenous receptor such as CX3CR1 is decreased (ca. 0.9 log(EC50)) see FIG. 6B) thus yielding an effect that can support a more effective drug with less side-effects. Both selectivity and potency is increased when comparing to a second peptide not comprising an optimized cleavage site.

Conclusion

The surprising effect on cell-killing selectivity is obtained by optimization of the cleavage site. Without being bound by any theory, this may be due to a difference in internalization and intracellular trafficking for a receptor encoded by a virus, such as the US28 receptor, versus an endogenous receptor, such as the CX3CR1 receptor.

REFERENCES

Hwang J et al., Cell. 1987 Jan. 16; 48(1):129-36;
Siegall C B et al., J Biol Chem. 1989 Aug. 25; 264(24): 14256-61).

The invention claimed is:

1. A fusion protein consisting of the amino acid sequence of SEQ ID NO: 6.

2. The fusion protein according to claim 1, wherein the fusion protein has increased potency against cells expressing US28 as compared to the potency against cells expressing CX3CR1.

3. The fusion protein according to claim 1, wherein the fusion protein has increased affinity for US28 as compared to the affinity for CX3CR1.

4. A pharmaceutical composition comprising the fusion protein according to claim 1 and a pharmaceutically acceptable carrier, diluent, or excipient.

5. The pharmaceutical composition according to claim 4, further comprising one or more further agents.

6. The pharmaceutical composition according to claim 5, wherein the agent is an immunosuppressive agent, anti-viral agent, or immunotherapy.

7. The pharmaceutical composition according to claim 6, wherein the anti-viral agent is valganciclovir, ganciclovir, cidofovir, leflunomide, prevymis, maribavir, or brincidofovir.

8. The pharmaceutical composition according to claim 6, wherein the immunotherapy is T cell therapy.

9. An isolated nucleic acid molecule encoding the fusion protein according to claim 1.

10. A vector comprising the nucleic acid molecule according to claim 9.

11. A recombinant host cell comprising the nucleic acid molecule according to claim 9 or the vector according to claim 10.

12. A method of treating a CMV infection or a CMV-associated disorder in an individual in need thereof, the method comprising administering a therapeutically effective amount of the fusion protein according to claim 1 or the pharmaceutical composition according to claim 4 to the individual.

13. The method according to claim 12, wherein the CMV infection is a latent or lytic CMV infection.

14. The method according to claim 12, wherein the CMV infection is an infection in an immune-compromised patient that is a HIV-patient, neonates and immunosuppressive patient, bone marrow transplant patient, solid organ transplant patient, immune therapy patient, cancer patient, intensive care patient, trauma patient, stem cell patient, gene therapy patient, cell therapy patient, geriatric patient, or multimorbid patient.

15. The method according to claim 12, wherein the CMV infection is an infection in a patient suffering from a coronary disease or a vascular disease.

16. The method according to claim 12, wherein the CMV-associated disorder is cytomegaloviral pneumonitis, cytomegaloviral hepatitis, cytomegaloviral pancreatitis, cytomegaloviral mononucleosis, CMV polyradiculomyelopathy, cytomegalic inclusion body disease, cytomegalovirus colitis, cytomegalovirus esophagitis, cytomegalovirus retinitis, Guillain-Barre syndrome, mucoepidermoid carcinoma, ulcerative colitis, graft versus host disease (GVHD), or solid organ transplant graft versus host disease (SOT-GVHD).

17. The method according to claim 12, wherein the individual is a human.

18. The method according to claim 17, wherein the human is an immunocompromised patient.

19. The method according to claim 17, wherein the human is a child or an adult.

20. The method according to claim 17, wherein the fusion protein or the pharmaceutical composition is administered one or more times to a human that is an immunocompromised patient or a human that is in need of a solid organ transplantation or a human that is in need of a hematopoietic stem cell transplantation.

21. A method of ex vivo treatment of a CMV infection of a solid organ for transplantation or a hematopoietic stem cell for transplantation, the method comprising contacting the fusion protein according to claim 1 or the pharmaceutical composition according to claim 4 with said solid organ or stem cell.

\* \* \* \* \*

SEQUENCE LISTING

```
<160> NUMBER OF SEQ ID NOS: 23

<210> SEQ ID NO 1
<211> LENGTH: 76
<212> TYPE: PRT
<213> ORGANISM: Homo sapiens

<400> SEQUENCE: 1

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
            35                  40                  45

Phe Cys Ala Asp Pro Lys Glu Gln Trp Val Lys Asp Ala Met Gln His
        50                  55                  60

Leu Asp Arg Gln Ala Ala Ala Leu Thr Arg Asn Gly
65                  70                  75

<210> SEQ ID NO 2
<211> LENGTH: 340
<212> TYPE: PRT
<213> ORGANISM: Pseudomonas aeruginosa

<400> SEQUENCE: 2

Gly Gly Ser Leu Ala Ala Leu Thr Ala His Gln Ala Cys His Leu Pro
1               5                   10                  15

Leu Glu Thr Phe Thr Arg His Arg Gln Arg Arg Gly Trp Glu Gln Leu
                20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
        50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Ser
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Gly Asp Ile Ser Phe Ser Thr Arg
        130                 135                 140

Gly Thr Gln Asn Trp Thr Val Glu Arg Leu Leu Gln Ala His Arg Gln
145                 150                 155                 160
```

-continued

```
Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
            195                 200                 205

Leu Ala Tyr Gly Tyr Ala Gln Asp Gln Glu Pro Asp Ala Arg Gly Arg
        210                 215                 220

Ile Arg Asn Gly Ala Leu Leu Arg Val Tyr Val Pro Arg Ser Ser Leu
225                 230                 235                 240

Pro Gly Phe Tyr Arg Thr Gly Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Glu Gly Gly Arg Leu Glu Thr Ile Leu
            275                 280                 285

Gly Trp Pro Leu Ala Glu Arg Thr Val Val Ile Pro Ser Ala Ile Pro
        290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro
            340

<210> SEQ ID NO 3
<211> LENGTH: 112
<212> TYPE: PRT
<213> ORGANISM: Pseudomonas aeruginosa

<400> SEQUENCE: 3

Gly Gly Ser Leu Ala Ala Leu Thr Ala His Gln Ala Cys His Leu Pro
1               5                   10                  15

Leu Glu Thr Phe Thr Arg His Arg Gln Arg Arg Gly Trp Glu Gln Leu
                20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
        50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Ser
                100                 105                 110

<210> SEQ ID NO 4
<211> LENGTH: 15
<212> TYPE: PRT
<213> ORGANISM: Pseudomonas aeruginosa

<400> SEQUENCE: 4

Gly Pro Ala Asp Ser Gly Asp Ala Leu Leu Glu Arg Asn Tyr Pro
1               5                   10                  15

<210> SEQ ID NO 5
<211> LENGTH: 213
```

```
<212> TYPE: PRT
<213> ORGANISM: Pseudomonas aeruginosa

<400> SEQUENCE: 5

Thr Gly Ala Glu Phe Leu Gly Asp Gly Gly Asp Ile Ser Phe Ser Thr
1               5                   10                  15

Arg Gly Thr Gln Asn Trp Thr Val Glu Arg Leu Leu Gln Ala His Arg
            20                  25                  30

Gln Leu Glu Glu Arg Gly Tyr Val Phe Val Gly Tyr His Gly Thr Phe
        35                  40                  45

Leu Glu Ala Ala Gln Ser Ile Val Phe Gly Gly Val Arg Ala Arg Ser
    50                  55                  60

Gln Asp Leu Asp Ala Ile Trp Arg Gly Phe Tyr Ile Ala Gly Asp Pro
65                  70                  75                  80

Ala Leu Ala Tyr Gly Tyr Ala Gln Asp Gln Glu Pro Asp Ala Arg Gly
                85                  90                  95

Arg Ile Arg Asn Gly Ala Leu Leu Arg Val Tyr Val Pro Arg Ser Ser
            100                 105                 110

Leu Pro Gly Phe Tyr Arg Thr Gly Leu Thr Leu Ala Ala Pro Glu Ala
            115                 120                 125

Ala Gly Glu Val Glu Arg Leu Ile Gly His Pro Leu Pro Leu Arg Leu
    130                 135                 140

Asp Ala Ile Thr Gly Pro Glu Glu Glu Gly Gly Arg Leu Glu Thr Ile
145                 150                 155                 160

Leu Gly Trp Pro Leu Ala Glu Arg Thr Val Val Ile Pro Ser Ala Ile
            165                 170                 175

Pro Thr Asp Pro Arg Asn Val Gly Gly Asp Leu Asp Pro Ser Ser Ile
            180                 185                 190

Pro Asp Lys Glu Gln Ala Ile Ser Ala Leu Pro Asp Tyr Ala Ser Gln
            195                 200                 205

Pro Gly Lys Pro Pro
    210

<210> SEQ ID NO 6
<211> LENGTH: 421
<212> TYPE: PRT
<213> ORGANISM: artificial sequence
<220> FEATURE:
<223> OTHER INFORMATION: fusion protein SYN002

<400> SEQUENCE: 6

Met Gln His His Gly Val Thr Lys Cys Asn Ile Thr Cys Ser Lys Met
1               5                   10                  15

Thr Ser Lys Ile Pro Val Ala Leu Leu Ile His Tyr Gln Gln Asn Gln
            20                  25                  30

Ala Ser Cys Gly Lys Arg Ala Ile Ile Leu Glu Thr Arg Gln His Arg
        35                  40                  45

Leu Ala Cys Ala Asp Pro Lys Glu Gln Trp Val Lys Asp Ala Met Gln
    50                  55                  60

His Leu Asp Arg Gln Ala Ala Ala Leu Thr Arg Asn Gly Gly Gly Ser
65                  70                  75                  80

Leu Ala Ala Leu Thr Ala His Gln Ala Cys His Leu Pro Leu Glu Thr
                85                  90                  95

Phe Thr Arg His Arg Gln Arg Arg Gly Trp Glu Gln Leu Glu Gln Cys
            100                 105                 110

Gly Tyr Pro Val Gln Arg Leu Val Ala Leu Tyr Leu Ala Ala Arg Leu
```

-continued

```
             115                 120                 125
Ser Trp Asn Gln Val Asp Gln Val Ile Arg Asn Ala Leu Ala Ser Pro
    130                 135                 140

Gly Ser Gly Gly Asp Leu Gly Glu Ala Ile Arg Glu Gln Pro Glu Gln
145                 150                 155                 160

Ala Arg Leu Ala Leu Thr Leu Ala Ala Ala Glu Ser Glu Arg Phe Val
                165                 170                 175

Arg Gln Gly Thr Gly Asn Asp Glu Ala Gly Ala Ala Ser Gly Pro Ala
                180                 185                 190

Asp Ser Gly Asp Ala Leu Leu Glu Arg Asn Tyr Pro Thr Gly Ala Glu
                195                 200                 205

Phe Leu Gly Asp Gly Gly Asp Ile Ser Phe Ser Thr Arg Gly Thr Gln
    210                 215                 220

Asn Trp Thr Val Glu Arg Leu Leu Gln Ala His Arg Gln Leu Glu Glu
225                 230                 235                 240

Arg Gly Tyr Val Phe Val Gly Tyr His Gly Thr Phe Leu Glu Ala Ala
                245                 250                 255

Gln Ser Ile Val Phe Gly Gly Val Arg Ala Arg Ser Gln Asp Leu Asp
                260                 265                 270

Ala Ile Trp Arg Gly Phe Tyr Ile Ala Gly Asp Pro Ala Leu Ala Tyr
                275                 280                 285

Gly Tyr Ala Gln Asp Gln Glu Pro Asp Ala Arg Gly Arg Ile Arg Asn
    290                 295                 300

Gly Ala Leu Leu Arg Val Tyr Val Pro Arg Ser Ser Leu Pro Gly Phe
305                 310                 315                 320

Tyr Arg Thr Gly Leu Thr Leu Ala Ala Pro Glu Ala Ala Gly Glu Val
                325                 330                 335

Glu Arg Leu Ile Gly His Pro Leu Pro Leu Arg Leu Asp Ala Ile Thr
                340                 345                 350

Gly Pro Glu Glu Glu Gly Gly Arg Leu Glu Thr Ile Leu Gly Trp Pro
                355                 360                 365

Leu Ala Glu Arg Thr Val Val Ile Pro Ser Ala Ile Pro Thr Asp Pro
    370                 375                 380

Arg Asn Val Gly Gly Asp Leu Asp Pro Ser Ser Ile Pro Asp Lys Glu
385                 390                 395                 400

Gln Ala Ile Ser Ala Leu Pro Asp Tyr Ala Ser Gln Pro Gly Lys Pro
                405                 410                 415

Pro Lys Asp Glu Leu
            420

<210> SEQ ID NO 7
<211> LENGTH: 397
<212> TYPE: PRT
<213> ORGANISM: Homo sapiens

<400> SEQUENCE: 7

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
                20                  25                  30

Asn Ile Thr Cys Ser Lys Met Thr Ser Lys Ile Pro Val Ala Leu Leu
            35                  40                  45

Ile His Tyr Gln Gln Asn Gln Ala Ser Cys Gly Lys Arg Ala Ile Ile
    50                  55                  60
```

```
Leu Glu Thr Arg Gln His Arg Leu Phe Cys Ala Asp Pro Lys Glu Gln
65              70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
            115                 120                 125

Pro Glu Ala Thr Gly Glu Ser Ser Leu Glu Pro Thr Pro Ser Ser
            130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
                180                 185                 190

Thr Ala Ala Thr Trp Gln Ser Ser Ala Pro His Gln Pro Gly Pro Ser
                195                 200                 205

Leu Trp Ala Glu Ala Lys Thr Ser Glu Ala Pro Ser Thr Gln Asp Pro
            210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
                260                 265                 270

Asp Ala Phe Gln Asp Trp Gly Pro Gly Ser Met Ala His Val Ser Val
                275                 280                 285

Val Pro Val Ser Ser Glu Gly Thr Pro Ser Arg Glu Pro Val Ala Ser
                290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
                340                 345                 350

Phe Cys Leu Gly Val Ala Met Phe Thr Tyr Gln Ser Leu Gln Gly Cys
                355                 360                 365

Pro Arg Lys Met Ala Gly Glu Met Ala Glu Gly Leu Arg Tyr Ile Pro
            370                 375                 380

Arg Ser Cys Gly Ser Asn Ser Tyr Val Leu Val Pro Val
385                 390                 395
```

```
<210> SEQ ID NO 8
<211> LENGTH: 4
<212> TYPE: PRT
<213> ORGANISM: Homo sapiens

<400> SEQUENCE: 8

Lys Asp Glu Leu
1

<210> SEQ ID NO 9
<211> LENGTH: 638
<212> TYPE: PRT
<213> ORGANISM: Pseudomonas aeruginosa
```

-continued

```
<400> SEQUENCE: 9

Met His Leu Thr Pro His Trp Ile Pro Leu Val Ala Ser Leu Gly Leu
1               5                   10                  15

Leu Ala Gly Gly Ser Phe Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
            115                 120                 125

Pro Ile Gly His Glu Lys Pro Ser Asn Ile Lys Val Phe Ile His Glu
        130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Ala Gln Pro Arg Arg
            195                 200                 205

Glu Lys Arg Trp Ser Glu Trp Ala Ser Gly Lys Val Leu Cys Leu Leu
        210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
            275                 280                 285

Ala Cys His Leu Pro Leu Glu Thr Phe Thr Arg His Arg Gln Pro Arg
        290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
        370                 375                 380

Ala Gly Ala Ala Ser Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
```

-continued

```
                405                410                415
Arg Asn Tyr Pro Thr Gly Ala Glu Phe Leu Gly Asp Gly Gly Asp Ile
            420                425                430

Ser Phe Ser Thr Arg Gly Thr Gln Asn Trp Thr Val Glu Arg Leu Leu
            435                440                445

Gln Ala His Arg Gln Leu Glu Glu Arg Gly Tyr Val Phe Val Gly Tyr
    450                455                460

His Gly Thr Phe Leu Glu Ala Ala Gln Ser Ile Val Phe Gly Gly Val
465                470                475                480

Arg Ala Arg Ser Gln Asp Leu Asp Ala Ile Trp Arg Gly Phe Tyr Ile
                485                490                495

Ala Gly Asp Pro Ala Leu Ala Tyr Gly Tyr Ala Gln Asp Gln Glu Pro
                500                505                510

Asp Ala Arg Gly Arg Ile Arg Asn Gly Ala Leu Leu Arg Val Tyr Val
                515                520                525

Pro Arg Ser Ser Leu Pro Gly Phe Tyr Arg Thr Gly Leu Thr Leu Ala
    530                535                540

Ala Pro Glu Ala Ala Gly Glu Val Glu Arg Leu Ile Gly His Pro Leu
545                550                555                560

Pro Leu Arg Leu Asp Ala Ile Thr Gly Pro Glu Glu Glu Gly Gly Arg
                565                570                575

Leu Glu Thr Ile Leu Gly Trp Pro Leu Ala Glu Arg Thr Val Val Ile
                580                585                590

Pro Ser Ala Ile Pro Thr Asp Pro Arg Asn Val Gly Gly Asp Leu Asp
            595                600                605

Pro Ser Ser Ile Pro Asp Lys Glu Gln Ala Ile Ser Ala Leu Pro Asp
    610                615                620

Tyr Ala Ser Gln Pro Gly Lys Pro Pro Arg Glu Asp Leu Lys
625                630                635

<210> SEQ ID NO 10
<211> LENGTH: 354
<212> TYPE: PRT
<213> ORGANISM: cytomegalovirus

<400> SEQUENCE: 10

Met Thr Pro Thr Thr Thr Thr Ala Glu Leu Thr Thr Glu Phe Asp Tyr
1               5                10                15

Asp Glu Ala Ala Thr Pro Cys Val Phe Thr Asp Val Leu Asn Gln Ser
            20                25                30

Lys Pro Val Thr Leu Phe Leu Tyr Gly Val Val Phe Leu Phe Gly Ser
            35                40                45

Ile Gly Asn Phe Leu Val Ile Phe Thr Ile Thr Trp Arg Arg Arg Ile
    50                55                60

Gln Cys Ser Gly Asp Val Tyr Phe Ile Asn Leu Ala Ala Ala Asp Leu
65                70                75                80

Leu Phe Val Cys Thr Leu Pro Leu Trp Met Gln Tyr Leu Leu Asp His
                85                90                95

Asn Ser Leu Ala Ser Val Pro Cys Thr Leu Leu Thr Ala Cys Phe Tyr
            100                105                110

Val Ala Met Phe Ala Ser Leu Cys Phe Ile Thr Glu Ile Ala Leu Asp
            115                120                125

Arg Tyr Tyr Ala Ile Val Tyr Met Arg Tyr Arg Pro Val Lys Gln Ala
            130                135                140
```

-continued

```
Cys Leu Phe Ser Ile Phe Trp Trp Ile Phe Ala Val Ile Ile Ala Ile
145                 150                 155                 160

Pro His Phe Met Val Val Thr Lys Lys Asp Asn Gln Cys Met Thr Asp
                165                 170                 175

Tyr Asp Tyr Leu Glu Val Ser Tyr Pro Ile Ile Leu Asn Val Glu Leu
            180                 185                 190

Met Leu Gly Ala Phe Val Ile Pro Leu Ser Val Ile Ser Tyr Cys Tyr
        195                 200                 205

Tyr Arg Ile Ser Arg Ile Val Ala Val Ser Gln Ser Arg His Lys Gly
    210                 215                 220

Arg Ile Val Arg Val Leu Ile Ala Val Val Leu Val Phe Ile Ile Phe
225                 230                 235                 240

Trp Leu Pro Tyr His Leu Thr Leu Phe Val Asp Thr Leu Lys Leu Leu
                245                 250                 255

Lys Trp Ile Ser Ser Ser Cys Glu Phe Glu Arg Ser Leu Lys Arg Ala
                260                 265                 270

Leu Ile Leu Thr Glu Ser Leu Ala Phe Cys His Cys Cys Leu Asn Pro
        275                 280                 285

Leu Leu Tyr Val Phe Val Gly Thr Lys Phe Arg Gln Glu Leu His Cys
    290                 295                 300

Leu Leu Ala Glu Phe Arg Gln Arg Leu Phe Ser Arg Asp Val Ser Trp
305                 310                 315                 320

Tyr His Ser Met Ser Phe Ser Arg Arg Ser Ser Pro Ser Arg Arg Glu
                325                 330                 335

Thr Ser Ser Asp Thr Leu Ser Asp Glu Val Cys Arg Val Ser Gln Ile
            340                 345                 350

Ile Pro
```

```
<210> SEQ ID NO 11
<211> LENGTH: 397
<212> TYPE: PRT
<213> ORGANISM: artificial sequence
<220> FEATURE:
<223> OTHER INFORMATION: fusion protein SYN000
```

```
<400> SEQUENCE: 11
```

```
Met Gln His His Gly Val Thr Lys Cys Asn Ile Thr Cys Ser Lys Met
1               5                   10                  15

Thr Ser Lys Ile Pro Val Ala Leu Leu Ile His Tyr Gln Gln Asn Gln
                20                  25                  30

Ala Ser Cys Gly Lys Arg Ala Ile Ile Leu Glu Thr Arg Gln His Arg
            35                  40                  45

Leu Phe Cys Ala Asp Pro Lys Glu Gln Trp Val Lys Asp Ala Met Gln
        50                  55                  60

His Leu Asp Arg Gln Ala Ala Ala Leu Thr Arg Asn Arg Gln Pro Arg
65                  70                  75                  80

Gly Trp Glu Gln Leu Glu Gln Ser Gly Tyr Pro Val Gln Arg Leu Val
                85                  90                  95

Ala Leu Tyr Leu Ala Ala Arg Leu Ser Trp Asn Gln Val Asp Gln Val
            100                 105                 110

Ile Arg Asn Ala Leu Ala Ser Pro Gly Ser Gly Gly Asp Leu Gly Glu
        115                 120                 125

Ala Ile Arg Glu Gln Pro Glu Gln Ala Arg Leu Ala Leu Thr Leu Ala
    130                 135                 140

Ala Ala Glu Ser Glu Arg Phe Val Arg Gln Gly Thr Gly Asn Asp Glu
```

-continued

```
145                150                155                160

Ala Gly Ala Ala Ser Gly Pro Ala Asp Ser Gly Asp Ala Leu Leu Glu
                 165                170                175

Arg Asn Tyr Pro Thr Gly Ala Glu Phe Leu Gly Asp Gly Gly Asp Ile
                 180                185                190

Ser Phe Ser Thr Arg Gly Thr Gln Asn Trp Thr Val Glu Arg Leu Leu
                 195                200                205

Gln Ala His Arg Gln Leu Glu Glu Arg Gly Tyr Val Phe Val Gly Tyr
     210                215                220

His Gly Thr Phe Leu Glu Ala Ala Gln Ser Ile Val Phe Gly Gly Val
225                230                235                240

Arg Ala Arg Ser Gln Asp Leu Asp Ala Ile Trp Arg Gly Phe Tyr Ile
                 245                250                255

Ala Gly Asp Pro Ala Leu Ala Tyr Gly Tyr Ala Gln Asp Gln Glu Pro
                 260                265                270

Asp Ala Arg Gly Arg Ile Arg Asn Gly Ala Leu Leu Arg Val Tyr Val
                 275                280                285

Pro Arg Ser Ser Leu Pro Gly Phe Tyr Arg Thr Gly Leu Thr Leu Ala
     290                295                300

Ala Pro Glu Ala Ala Gly Glu Val Glu Arg Leu Ile Gly His Pro Leu
305                310                315                320

Pro Leu Arg Leu Asp Ala Ile Thr Gly Pro Glu Glu Glu Gly Gly Arg
                 325                330                335

Leu Glu Thr Ile Leu Gly Trp Pro Leu Ala Glu Arg Thr Val Val Ile
                 340                345                350

Pro Ser Ala Ile Pro Thr Asp Pro Arg Asn Val Gly Gly Asp Leu Asp
                 355                360                365

Pro Ser Ser Ile Pro Asp Lys Glu Gln Ala Ile Ser Ala Leu Pro Asp
     370                375                380

Tyr Ala Ser Gln Pro Gly Lys Pro Pro Lys Asp Glu Leu
385                390                395
```

<210> SEQ ID NO 12
<211> LENGTH: 396
<212> TYPE: PRT
<213> ORGANISM: artificial sequence
<220> FEATURE:
<223> OTHER INFORMATION: fusion protein SYN001

<400> SEQUENCE: 12

```
Met Gln His His Gly Val Thr Lys Cys Asn Ile Thr Cys Ser Lys Met
1                5                  10                 15

Thr Ser Lys Ile Pro Val Ala Leu Leu Ile His Tyr Gln Gln Asn Gln
                 20                 25                 30

Ala Ser Cys Gly Lys Arg Ala Ile Ile Leu Glu Thr Arg Gln His Arg
                 35                 40                 45

Leu Ala Cys Ala Asp Pro Lys Glu Gln Trp Val Lys Asp Ala Met Gln
     50                 55                 60

His Leu Asp Arg Gln Ala Ala Ala Leu Thr Arg Asn Arg Gln Pro Arg
65                 70                 75                 80

Gly Trp Glu Gln Leu Glu Gln Ser Gly Tyr Pro Val Gln Arg Leu Val
                 85                 90                 95

Ala Leu Tyr Leu Ala Ala Arg Leu Ser Trp Asn Gln Val Asp Gln Val
                 100                105                110

Ile Arg Asn Ala Leu Ala Ser Pro Gly Ser Gly Gly Asp Leu Gly Glu
```

-continued

```
             115                 120                 125
Ala Ile Arg Glu Gln Pro Glu Gln Ala Arg Leu Ala Leu Thr Leu Ala
    130                 135                 140

Ala Ala Glu Ser Glu Arg Phe Val Arg Gln Gly Thr Gly Asn Asp Glu
145                 150                 155                 160

Ala Gly Ala Ala Ser Gly Pro Ala Asp Ser Gly Asp Ala Leu Leu Glu
                165                 170                 175

Arg Asn Tyr Pro Thr Gly Ala Glu Phe Leu Gly Asp Gly Gly Asp Ile
            180                 185                 190

Ser Phe Ser Thr Arg Gly Thr Gln Asn Trp Thr Val Glu Arg Leu Leu
            195                 200                 205

Gln Ala His Arg Gln Leu Glu Glu Arg Gly Tyr Val Phe Val Gly Tyr
    210                 215                 220

His Gly Thr Phe Leu Glu Ala Ala Gln Ser Ile Val Phe Gly Gly Val
225                 230                 235                 240

Arg Ala Arg Ser Gln Asp Leu Asp Ala Ile Trp Arg Gly Phe Tyr Ile
                245                 250                 255

Ala Gly Asp Pro Ala Leu Ala Tyr Gly Tyr Ala Gln Asp Gln Glu Pro
                260                 265                 270

Asp Ala Arg Gly Arg Ile Arg Asn Gly Ala Leu Leu Arg Val Tyr Val
            275                 280                 285

Pro Arg Ser Ser Leu Pro Gly Phe Tyr Arg Thr Gly Leu Thr Leu Ala
    290                 295                 300

Ala Pro Glu Ala Ala Gly Glu Val Glu Arg Leu Ile Gly His Pro Leu
305                 310                 315                 320

Pro Leu Arg Leu Asp Ala Ile Thr Gly Pro Glu Glu Glu Gly Gly Arg
                325                 330                 335

Leu Glu Thr Ile Leu Gly Trp Pro Leu Ala Glu Arg Thr Val Val Ile
            340                 345                 350

Pro Ser Ala Ile Pro Thr Asp Pro Arg Asn Val Gly Gly Asp Leu Asp
            355                 360                 365

Pro Ser Ser Ile Pro Asp Lys Glu Gln Ala Ile Ser Ala Leu Pro Asp
    370                 375                 380

Tyr Ala Ser Gln Pro Gly Lys Pro Pro Lys Asp Glu
385                 390                 395

<210> SEQ ID NO 13
<211> LENGTH: 421
<212> TYPE: PRT
<213> ORGANISM: artificial sequence
<220> FEATURE:
<223> OTHER INFORMATION: fusion protein SYN014

<400> SEQUENCE: 13

Met Gln His His Gly Val Thr Lys Cys Asn Ile Thr Cys Ser Lys Met
1               5                   10                  15

Thr Ser Lys Ile Pro Val Ala Leu Leu Ile His Tyr Gln Gln Asn Gln
            20                  25                  30

Ala Ser Cys Gly Lys Arg Ala Ile Ile Leu Glu Thr Arg Gln His Arg
            35                  40                  45

Leu Phe Cys Ala Asp Pro Lys Glu Gln Trp Val Lys Asp Ala Met Gln
    50                  55                  60

His Leu Asp Arg Gln Ala Ala Ala Leu Thr Arg Asn Gly Gly Gly Ser
65                  70                  75                  80

Leu Ala Ala Leu Thr Ala His Gln Ala Cys His Leu Pro Leu Glu Thr
```

-continued

```
                  85              90              95

Phe Thr Arg His Arg Gln Arg Arg Gly Trp Glu Gln Leu Glu Gln Cys
            100             105             110

Gly Tyr Pro Val Gln Arg Leu Val Ala Leu Tyr Leu Ala Ala Arg Leu
            115             120             125

Ser Trp Asn Gln Val Asp Gln Val Ile Arg Asn Ala Leu Ala Ser Pro
        130             135             140

Gly Ser Gly Gly Asp Leu Gly Glu Ala Ile Arg Glu Gln Pro Glu Gln
145             150             155             160

Ala Arg Leu Ala Leu Thr Leu Ala Ala Ala Glu Ser Glu Arg Phe Val
            165             170             175

Arg Gln Gly Thr Gly Asn Asp Glu Ala Gly Ala Ala Ser Gly Pro Ala
            180             185             190

Asp Ser Gly Asp Ala Leu Leu Glu Arg Asn Tyr Pro Thr Gly Ala Glu
        195             200             205

Phe Leu Gly Asp Gly Gly Asp Ile Ser Phe Ser Thr Arg Gly Thr Gln
    210             215             220

Asn Trp Thr Val Glu Arg Leu Leu Gln Ala His Arg Gln Leu Glu Glu
225             230             235             240

Arg Gly Tyr Val Phe Val Gly Tyr His Gly Thr Phe Leu Glu Ala Ala
            245             250             255

Gln Ser Ile Val Phe Gly Gly Val Arg Ala Arg Ser Gln Asp Leu Asp
            260             265             270

Ala Ile Trp Arg Gly Phe Tyr Ile Ala Gly Asp Pro Ala Leu Ala Tyr
            275             280             285

Gly Tyr Ala Gln Asp Gln Glu Pro Asp Ala Arg Gly Arg Ile Arg Asn
        290             295             300

Gly Ala Leu Leu Arg Val Tyr Val Pro Arg Ser Ser Leu Pro Gly Phe
305             310             315             320

Tyr Arg Thr Gly Leu Thr Leu Ala Ala Pro Glu Ala Ala Gly Glu Val
            325             330             335

Glu Arg Leu Ile Gly His Pro Leu Pro Leu Arg Leu Asp Ala Ile Thr
            340             345             350

Gly Pro Glu Glu Glu Gly Gly Arg Leu Glu Thr Ile Leu Gly Trp Pro
        355             360             365

Leu Ala Glu Arg Thr Val Val Ile Pro Ser Ala Ile Pro Thr Asp Pro
    370             375             380

Arg Asn Val Gly Gly Asp Leu Asp Pro Ser Ser Ile Pro Asp Lys Glu
385             390             395             400

Gln Ala Ile Ser Ala Leu Pro Asp Tyr Ala Ser Gln Pro Gly Lys Pro
            405             410             415

Pro Lys Asp Glu Leu
            420

<210> SEQ ID NO 14
<211> LENGTH: 421
<212> TYPE: PRT
<213> ORGANISM: artificial sequence
<220> FEATURE:
<223> OTHER INFORMATION: fusion protein SYN016

<400> SEQUENCE: 14

Met Gln His His Gly Val Thr Lys Cys Asn Ile Thr Cys Ser Lys Met
1               5               10              15

Thr Ser Lys Ile Pro Val Ala Leu Leu Ile His Tyr Gln Gln Asn Gln
```

-continued

```
                20                25                30

Ala Ser Cys Gly Lys Arg Ala Ile Ile Leu Glu Thr Arg Gln His Arg
        35                40                45

Leu Ala Cys Ala Asp Pro Lys Glu Gln Trp Val Lys Asp Ala Met Gln
    50                55                60

His Leu Asp Arg Gln Ala Ala Leu Thr Arg Asn Gly Gly Gly Ser
65                70                75                80

Leu Ala Ala Leu Thr Ala His Gln Ala Cys His Leu Pro Leu Glu Thr
                85                90                95

Phe Thr Arg His Arg Gln Pro Arg Gly Trp Glu Gln Leu Glu Gln Cys
            100                105                110

Gly Tyr Pro Val Gln Arg Leu Val Ala Leu Tyr Leu Ala Ala Arg Leu
        115                120                125

Ser Trp Asn Gln Val Asp Gln Val Ile Arg Asn Ala Leu Ala Ser Pro
        130                135                140

Gly Ser Gly Gly Asp Leu Gly Glu Ala Ile Arg Glu Gln Pro Glu Gln
145                150                155                160

Ala Arg Leu Ala Leu Thr Leu Ala Ala Ala Glu Ser Glu Arg Phe Val
                165                170                175

Arg Gln Gly Thr Gly Asn Asp Glu Ala Gly Ala Ala Ser Gly Pro Ala
                180                185                190

Asp Ser Gly Asp Ala Leu Leu Glu Arg Asn Tyr Pro Thr Gly Ala Glu
                195                200                205

Phe Leu Gly Asp Gly Gly Asp Ile Ser Phe Ser Thr Arg Gly Thr Gln
        210                215                220

Asn Trp Thr Val Glu Arg Leu Leu Gln Ala His Arg Gln Leu Glu Glu
225                230                235                240

Arg Gly Tyr Val Phe Val Gly Tyr His Gly Thr Phe Leu Glu Ala Ala
                245                250                255

Gln Ser Ile Val Phe Gly Gly Val Arg Ala Arg Ser Gln Asp Leu Asp
                260                265                270

Ala Ile Trp Arg Gly Phe Tyr Ile Ala Gly Asp Pro Ala Leu Ala Tyr
            275                280                285

Gly Tyr Ala Gln Asp Gln Glu Pro Asp Ala Arg Gly Arg Ile Arg Asn
        290                295                300

Gly Ala Leu Leu Arg Val Tyr Val Pro Arg Ser Ser Leu Pro Gly Phe
305                310                315                320

Tyr Arg Thr Gly Leu Thr Leu Ala Ala Pro Glu Ala Ala Gly Glu Val
                325                330                335

Glu Arg Leu Ile Gly His Pro Leu Pro Leu Arg Leu Asp Ala Ile Thr
                340                345                350

Gly Pro Glu Glu Glu Gly Gly Arg Leu Glu Thr Ile Leu Gly Trp Pro
            355                360                365

Leu Ala Glu Arg Thr Val Val Ile Pro Ser Ala Ile Pro Thr Asp Pro
        370                375                380

Arg Asn Val Gly Gly Asp Leu Asp Pro Ser Ser Ile Pro Asp Lys Glu
385                390                395                400

Gln Ala Ile Ser Ala Leu Pro Asp Tyr Ala Ser Gln Pro Gly Lys Pro
                405                410                415

Pro Lys Asp Glu Leu
            420
```

<210> SEQ ID NO 15

-continued

<211> LENGTH: 421
<212> TYPE: PRT
<213> ORGANISM: artificial sequence
<220> FEATURE:
<223> OTHER INFORMATION: fusion protein SYN017

<400> SEQUENCE: 15

Met Gln His His Gly Val Thr Lys Cys Asn Ile Thr Cys Ser Lys Met
1               5                   10                  15

Thr Ser Lys Ile Pro Val Ala Leu Leu Ile His Tyr Gln Gln Asn Gln
            20                  25                  30

Ala Ser Cys Gly Lys Arg Ala Ile Ile Leu Glu Thr Arg Gln His Arg
        35                  40                  45

Leu Phe Cys Ala Asp Pro Lys Glu Gln Trp Val Lys Asp Ala Met Gln
    50                  55                  60

His Leu Asp Arg Gln Ala Ala Ala Leu Thr Arg Asn Gly Gly Gly Ser
65                  70                  75                  80

Leu Ala Ala Leu Thr Ala His Gln Ala Cys His Leu Pro Leu Glu Thr
                85                  90                  95

Phe Thr Arg His Arg Gln Pro Arg Gly Trp Glu Gln Leu Glu Gln Cys
            100                 105                 110

Gly Tyr Pro Val Gln Arg Leu Val Ala Leu Tyr Leu Ala Ala Arg Leu
        115                 120                 125

Ser Trp Asn Gln Val Asp Gln Val Ile Arg Asn Ala Leu Ala Ser Pro
    130                 135                 140

Gly Ser Gly Gly Asp Leu Gly Glu Ala Ile Arg Glu Gln Pro Glu Gln
145                 150                 155                 160

Ala Arg Leu Ala Leu Thr Leu Ala Ala Ala Glu Ser Glu Arg Phe Val
                165                 170                 175

Arg Gln Gly Thr Gly Asn Asp Glu Ala Gly Ala Ala Ser Gly Pro Ala
            180                 185                 190

Asp Ser Gly Asp Ala Leu Leu Glu Arg Asn Tyr Pro Thr Gly Ala Glu
        195                 200                 205

Phe Leu Gly Asp Gly Gly Asp Ile Ser Phe Ser Thr Arg Gly Thr Gln
    210                 215                 220

Asn Trp Thr Val Glu Arg Leu Leu Gln Ala His Arg Gln Leu Glu Glu
225                 230                 235                 240

Arg Gly Tyr Val Phe Val Gly Tyr His Gly Thr Phe Leu Glu Ala Ala
                245                 250                 255

Gln Ser Ile Val Phe Gly Gly Val Arg Ala Arg Ser Gln Asp Leu Asp
            260                 265                 270

Ala Ile Trp Arg Gly Phe Tyr Ile Ala Gly Asp Pro Ala Leu Ala Tyr
        275                 280                 285

Gly Tyr Ala Gln Asp Gln Glu Pro Asp Ala Arg Gly Arg Ile Arg Asn
    290                 295                 300

Gly Ala Leu Leu Arg Val Tyr Val Pro Arg Ser Ser Leu Pro Gly Phe
305                 310                 315                 320

Tyr Arg Thr Gly Leu Thr Leu Ala Ala Pro Glu Ala Ala Gly Glu Val
                325                 330                 335

Glu Arg Leu Ile Gly His Pro Leu Pro Leu Arg Leu Asp Ala Ile Thr
            340                 345                 350

Gly Pro Glu Glu Glu Gly Gly Arg Leu Glu Thr Ile Leu Gly Trp Pro
        355                 360                 365

Leu Ala Glu Arg Thr Val Val Ile Pro Ser Ala Ile Pro Thr Asp Pro
    370                 375                 380

```
Arg Asn Val Gly Gly Asp Leu Asp Pro Ser Ser Ile Pro Asp Lys Glu
385                 390                 395                 400

Gln Ala Ile Ser Ala Leu Pro Asp Tyr Ala Ser Gln Pro Gly Lys Pro
                405                 410                 415

Pro Lys Asp Glu Leu
            420

<210> SEQ ID NO 16
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 16

Arg Gln Arg Arg
1

<210> SEQ ID NO 17
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 17

Arg Gln Lys Arg
1

<210> SEQ ID NO 18
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 18

Arg Ser Lys Arg
1

<210> SEQ ID NO 19
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 19

Arg Ser Arg Arg
1
```

```
<210> SEQ ID NO 20
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 20

Arg Thr Lys Arg
1

<210> SEQ ID NO 21
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 21

Arg Thr Arg Arg
1

<210> SEQ ID NO 22
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 22

Arg Asn Lys Arg
1

<210> SEQ ID NO 23
<211> LENGTH: 4
<212> TYPE: PRT
<213> ORGANISM: Artificial Sequence
<220> FEATURE:
<223> OTHER INFORMATION: cleavage site
<220> FEATURE:
<221> NAME/KEY: PEPTIDE
<222> LOCATION: (1)..(4)
<223> OTHER INFORMATION: cleavage site

<400> SEQUENCE: 23

Arg Asn Arg Arg
1
```